United States Patent
Waas et al.

(10) Patent No.: US 8,491,742 B2
(45) Date of Patent: *Jul. 23, 2013

(54) METHOD FOR EMBOSSING AN ABSORBENT ARTICLE USING A SEGMENTED ANVIL

(75) Inventors: Steve J. Waas, Deerfield Township, OH (US); Gregory J. Wilson, Mason, OH (US); Rong Deng, Mason, OH (US); Valerie J. Henderson, Liberty Township, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 216 days.

This patent is subject to a terminal disclaimer.

(21) Appl. No.: 12/913,936

(22) Filed: Oct. 28, 2010

(65) Prior Publication Data

US 2012/0103505 A1 May 3, 2012

(51) Int. Cl.
*B29C 59/04* (2006.01)
*A61F 13/47* (2006.01)

(52) U.S. Cl.
USPC .......................... 156/209; 156/292; 156/293

(58) Field of Classification Search
None
See application file for complete search history.

(56) References Cited

U.S. PATENT DOCUMENTS

| | | | |
|---|---|---|---|
| 4,256,526 A | 3/1981 | McDaniel | |
| 4,687,137 A | 8/1987 | Boger et al. | |
| 4,795,455 A | 1/1989 | Luceri et al. | |
| 4,874,451 A | 10/1989 | Boger et al. | |
| 4,960,477 A | 10/1990 | Mesek | |
| 5,421,941 A | 6/1995 | Allen et al. | |
| 5,423,935 A | 6/1995 | Benecke et al. | |
| 5,560,878 A | 10/1996 | Dragoo et al. | |
| 5,674,341 A * | 10/1997 | Ng | 156/234 |
| 5,681,305 A | 10/1997 | Korpman | |
| 5,683,752 A | 11/1997 | Popp et al. | |
| 5,700,322 A | 12/1997 | Fort | |
| 5,792,311 A | 8/1998 | Ng | |
| 5,795,344 A | 8/1998 | Chappell | |
| 5,830,296 A * | 11/1998 | Emenaker et al. | 156/219 |
| 5,941,861 A | 8/1999 | Ng | |
| 6,517,525 B1 | 2/2003 | Berthou et al. | |
| 6,563,013 B1 | 5/2003 | Murota | |
| 6,613,175 B1 | 9/2003 | Moscherosch et al. | |
| 6,867,345 B2 | 3/2005 | Shimoe et al. | |
| 7,048,885 B2 | 5/2006 | Weiher et al. | |
| 7,078,583 B2 | 7/2006 | Kudo et al. | |
| 7,247,215 B2 | 7/2007 | Schewe et al. | |
| 7,435,926 B2 | 10/2008 | Jafarian-Tehrani | |
| 7,550,646 B2 | 6/2009 | Tamura et al. | |

(Continued)

FOREIGN PATENT DOCUMENTS

| WO | WO 97/40804 A1 | 11/1997 |
|---|---|---|
| WO | WO 98/27908 A1 | 7/1998 |
| WO | WO-2010068150 A1 | 6/2010 |

OTHER PUBLICATIONS

International Search Report dated Mar. 19, 2012, PCT/US2011/058097, 8 pages.

*Primary Examiner* — Barbara J Musser
(74) *Attorney, Agent, or Firm* — Andrew J. Hagerty; Megan C. Hymore; James E. Oehlenschlager

(57) ABSTRACT

A method for embossing an absorbent article using a segmented anvil and attaching a release paper to a backsheet having depressed regions.

23 Claims, 21 Drawing Sheets

U.S. PATENT DOCUMENTS

| | | |
|---|---|---|
| 2004/0127875 A1 | 7/2004 | Hammons et al. |
| 2006/0155253 A1 | 7/2006 | Dziezok et al. |
| 2008/0281287 A1 | 11/2008 | Marcelo et al. |
| 2009/0137977 A1 | 5/2009 | Fukae et al. |
| 2012/0103504 A1 | 5/2012 | Deng et al. |
| 2012/0109093 A1 | 5/2012 | Wilson et al. |

* cited by examiner

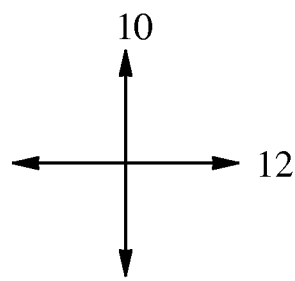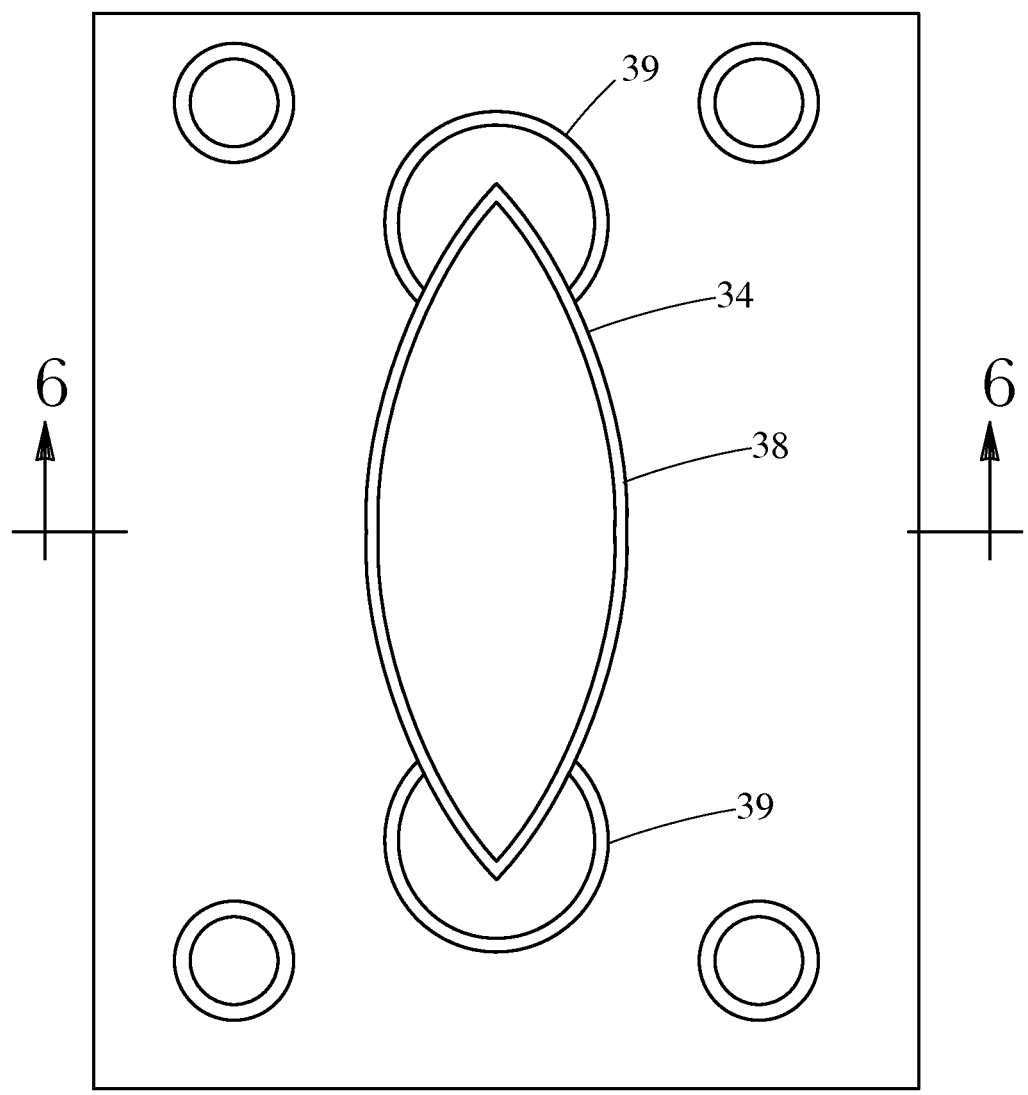
Fig. 5

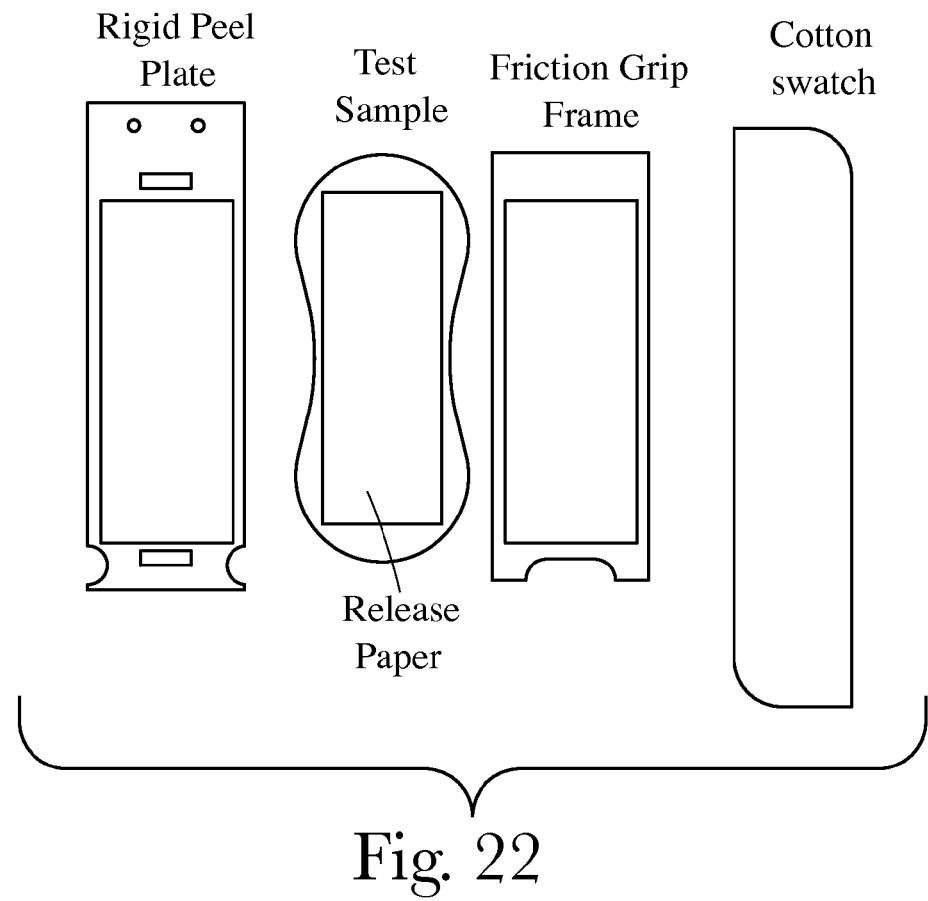
Fig. 22
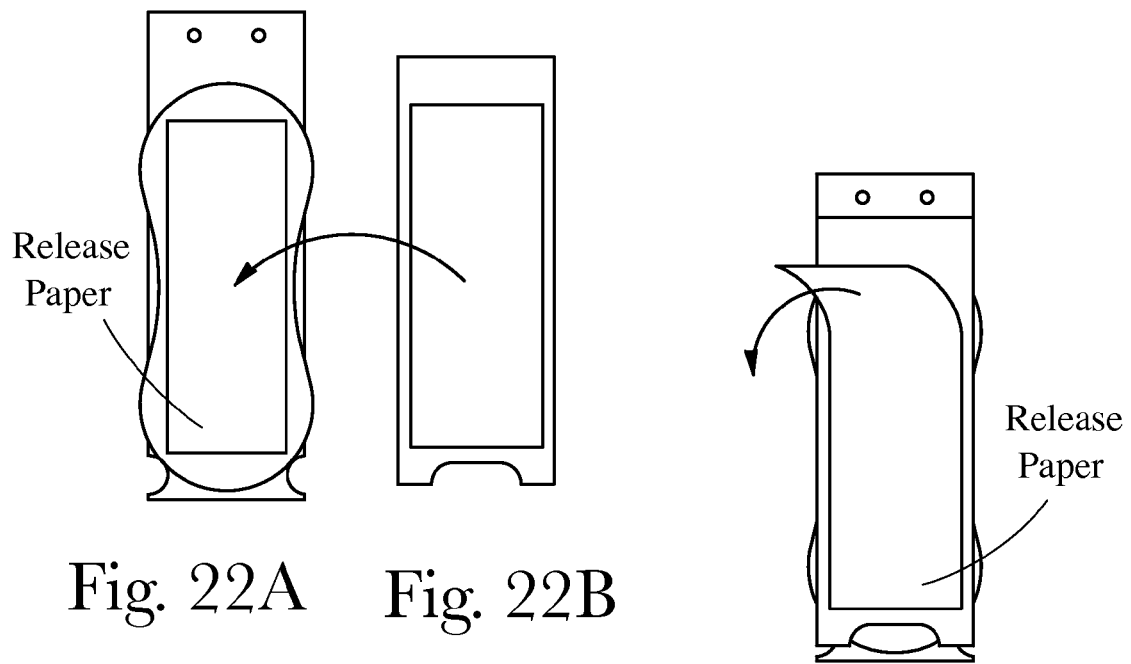
Fig. 22A  Fig. 22B
Fig. 22C

METHOD FOR EMBOSSING AN ABSORBENT ARTICLE USING A SEGMENTED ANVIL

FIELD OF THE INVENTION

The invention relates to a method for embossing an absorbent article using a segmented anvil member and the application of an adhesive to the absorbent article.

BACKGROUND OF THE INVENTION

Rotary embossing systems have traditionally been used to emboss the webs that form absorbent articles. Typical embossing systems have included rotary embossing rolls and cooperating, rotary anvil rolls. Different embossment dies can be fixed to rotary embossing rolls to produce a variety of desired embossment regions for absorbent articles.

A typical embossed absorbent article, such as feminine sanitary napkin comprises a topsheet, absorbent core and backsheet, the backsheet is usually attached to the top sheet prior to the embossment of the topsheet and absorbent core. The attachment of the backsheet to the absorbent core prior to embossment has limited the depth of the embossment regions, as if the embossment is too deep the backsheet may be damaged during the embossment process, such as by cutting or tearing the backsheet. The backsheet is typically made of a water resistant material, such as plastic, which makes the backsheet more vulnerable to damage, than for example a non-woven web. In addition to harming the appearance of the absorbent article, damage to the backsheet can compromise the effectiveness of the absorbent article, as a damaged backsheet could allow absorbed fluids to leave the absorbent article and contact the skin or clothes of a wearer. It has also been difficult to emboss an absorbent article to a uniform depth along the entire embossment region. This is especially true when the embossment region has one or more closed ends, for example embossment regions in the shape of a peanut or oval. The separation distance between the embossing roll and rotary anvil roll increases at the ends of the ends of the embossment regions resulting in less pressure being allied by the embossing dies, and a corresponding reduction in depth in the embossment regions. The lack of pressure is increased when the ends of the embossment region are closed, as the pressure is spread out along an even greater surface area.

Deep channel embossments in an absorbent article provide improved fit of the absorbent article to the wearer's body, which is important in delivering superior protection performance. Deep channel embossments also provide a pleasant feminine design to the wearer. Further the embossed region also serves as a fluid barrier that prevents fluid from running off to the side of the absorbent article.

In addition, the process of forming deep channel embossments can produce embossment regions, not only in the surface contacted by the rotary embossing rolls (typically the body facing surface including the topsheet), but also in the opposing surface (typically the garment facing surface). The garment facing surface of the absorbent core is the surface that will come in contact with the backsheet. The backsheet will often conform to the embossments present in the garment facing surface of the absorbent core, resulting in an uneven surface in the backsheet. The uneven surface of the backsheet causes problems when trying to attach release paper to the surface of the backsheet. Adhesive is usually applied to the release paper first and then the release paper is contacted with the backsheet, such that the adhesive holds the release paper to the backsheet until use. However, as there are valleys present in the backsheet due to the embossments the adhesive present on the release paper will bridge these valleys, and consequently the adhesive will not come into direct contact with the backsheet. The irregular adhesive contact leads to several problems, including poor adhesive transfer from the release paper to the backsheet allowing adhesive to remain on the release paper or reducing its effectiveness of remaining on the absorbent article and transferring to an undesired surface, such as a user's panties. Another problem is that when users peels the release paper off the pads, the adhesive strings (situation similar to gum sticking/string to your shoe when you step on gum and lift your foot) between the backsheet and release paper. The adhesive could get to a user's finger and snap back to either release paper or backsheet. These are all undesired usage experience for the users. A further complication is that the adhesive not in contact with the backsheet will not transfer from the release paper making use of the absorbent article more difficult, as the release paper can now stick to unwanted surfaces, complicating attachment of the absorbent article. In addition direct application of an adhesive to the backsheet, will not apply adhesive to the valleys formed in the backsheet resulting in the same problems with the release paper.

A method of forming deep channel embossments is needed that prevents damage to the backsheet of the absorbent article, provides a substantially consistent depth to an embossment region, and allows for proper adherence of the release paper to the backsheet.

SUMMARY OF THE INVENTION

A method for embossing an absorbent article is provided that comprises the steps of providing a topsheet; providing an absorbent core having a garment facing side and a body facing side and positioning the body facing side of the absorbent core on the topsheet; moving the topsheet and absorbent core in a machine direction; operatively contacting the garment facing side of the absorbent core with a segmented anvil member and the topsheet with an embossing member of a rotary embossing device to form an embossment region in at least a portion of the topsheet and body facing side of the absorbent core and a depression region in the garment facing side of the absorbent core; contacting a backsheet with the garment facing side of the absorbent core having a depression region; applying adhesive in a pattern to the backsheet using a non-contact die means; and operatively attaching a release paper to the backsheet.

A method for embossing an absorbent article is provided that comprises the steps of providing a topsheet; providing an absorbent core having a garment facing side and a body facing side and positioning the body facing side of the absorbent core on the topsheet; moving the topsheet and absorbent core in a machine direction; operatively contacting the garment facing side of the absorbent core with a segmented anvil member and the topsheet with an embossment member of a rotary embossing device to form an embossment region in at least a portion of the topsheet and body facing side of the absorbent core and a depression region in the garment facing side of the absorbent core; contacting a backsheet with the garment facing side of the absorbent core having a depression region; applying adhesive in a pattern to the backsheet using a non-contact die means; wherein the application of adhesive comprises the steps of extruding adhesive from an extrusion outlet; impinging a flow of air from the extrusion outlet at an angle unto the extruding adhesive; depositing extruded adhesive onto the backsheet; and operatively attaching a release paper to the backsheet.

BRIEF DESCRIPTION OF THE DRAWINGS

FIG. 5 is a top view of an embossing member.

FIGS. 22 and 22A-22F show a diagram illustrating the preparation of a sample.

DETAILED DESCRIPTION OF THE INVENTION

The present invention relates to a method for producing an embossed absorbent article, such as a feminine sanitary napkin. The method includes moving a topsheet and an absorbent core having a body facing surface and a garment facing surface, in the machine direction, such that they are embossed by a rotary embossing device having one or more embossing members in operative contact with a rotary segmented anvil member. The embossing members contact the body facing surface of the topsheet, forming embossment regions in the body facing surface of the topsheet and absorbent core and forming depression regions corresponding to the embossment regions in the garment facing surface of the absorbent core. Following embossment a backsheet covers the garment facing surface of the absorbent core web. Adhesive is applied to the backsheet using a non-contact method, such as a spray, and a release paper is then contacted with the adhesive coated surface of the backsheet.

As used herein, the phrase "absorbent article" refers to devices which absorb and contain body liquids, and more specifically refers to devices which may be placed against or near the skin to absorb and contain the various liquids, such as those discharged from the body. In typical use the absorbent articles are not intended to be laundered or otherwise restored or reused after a single use. Examples of absorbent articles include, but are not limited to: personal care absorbent products, such as: feminine hygiene products, for example feminine sanitary napkins, pantiliners, tampons, interlabial devices and the like; infant diapers; children's training pants; adult incontinence products; as well as absorbent wipes.

Absorbent articles, and their individual components, such as a liquid pervious topsheet, a substantially liquid impervious backsheet joined to the topsheet, and an absorbent core positioned and held between the topsheet and the backsheet, have a body facing surface and a garment facing surface. As used herein, "body-facing surface" means that surface of the article or component which is intended to be disposed toward or placed adjacent to the body of the wearer during ordinary use, while the "garment facing surface" is on the opposite side, and is intended to be disposed to face away from the wearer's body during ordinary use. The garment facing surface may be arranged to face toward or placed adjacent to the wearer's undergarments when the absorbent article is worn. In general the topsheet is operatively permeable to the liquids that are intended to be held or stored by the absorbent article, and the backsheet may be substantially impermeable or otherwise operatively impermeable to the intended liquids. The absorbent article may also include other components, such as a secondary topsheet, liquid wicking layers, liquid distribution layers, barrier layers, and the like, as well as combinations thereof.

Figure 1:
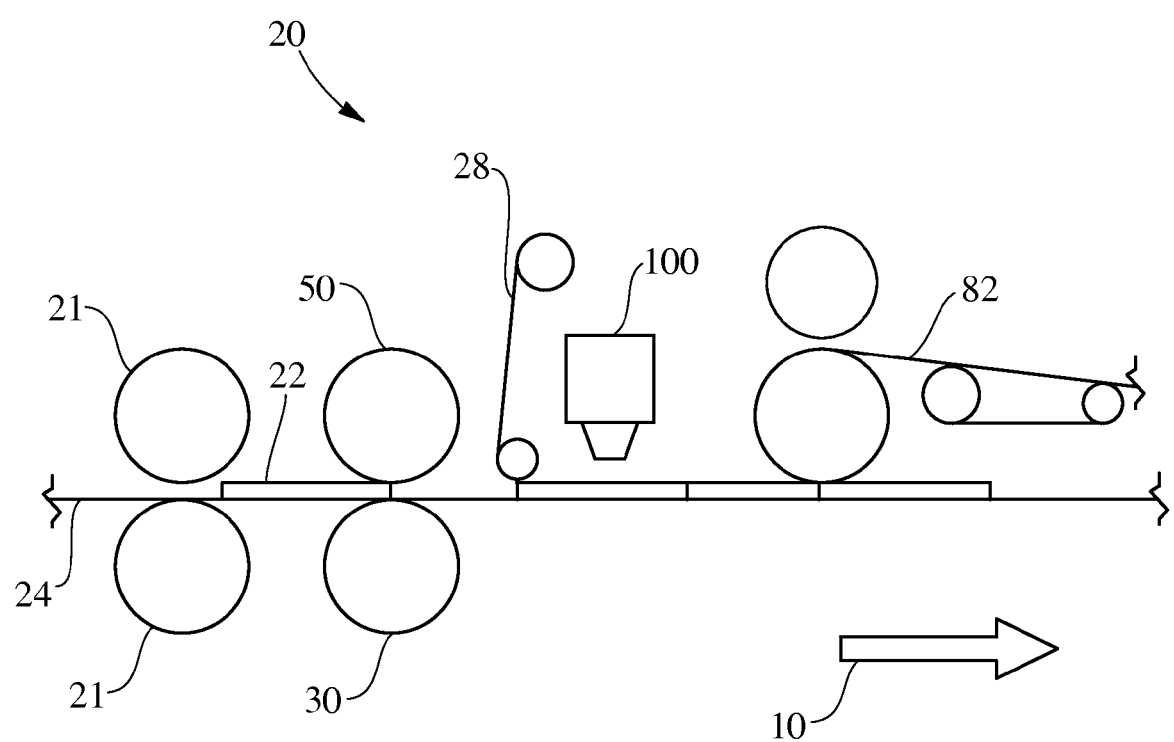
FIG. 1 shows a schematic side view of an embodiment of the present invention for embossing an absorbent core.
Figure 2:
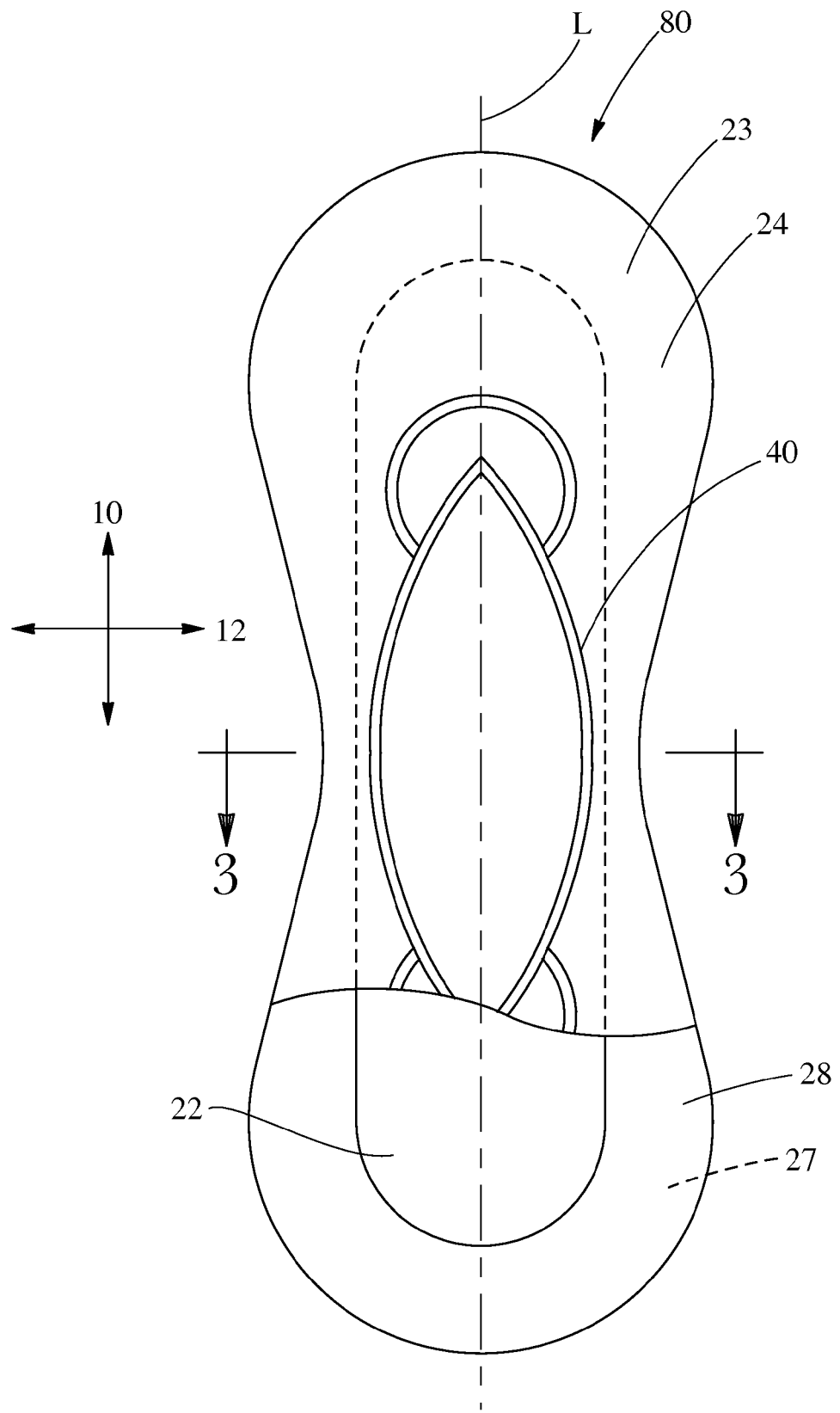
FIG. 2 is a top down partial cut-away view of the body facing surface of a feminine sanitary napkin having an embossment region.

With reference to FIGS. 1 and 2, the method of the invention can have a machine-direction 10 which extends longitudinally, and a lateral cross-direction 12 which extends transversely. The machine-direction 10 is the direction along which a particular component or material is transported along and through a particular position of the method. The cross-direction 12 lies generally within the plane of the material being transported through the method, and is aligned perpendicular to the machine-direction 10. Accordingly, in the view of the arrangement representatively shown in FIG. 1, the cross-direction 12 extends perpendicular to the plane of the sheet of the drawing.

Figure 3:
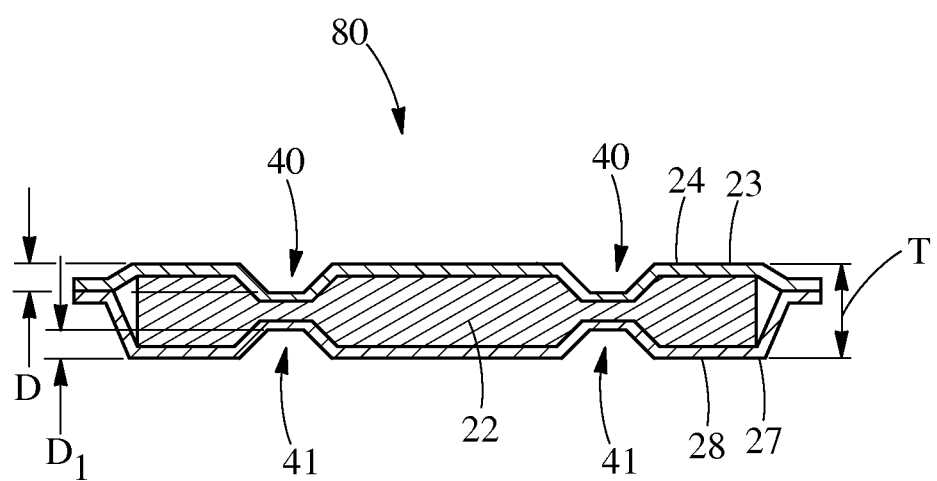
FIG. 3 is a view of a cross-section of the feminine sanitary napkin of FIG. 2 along the cross-directional line 3-3.
Figure 4:
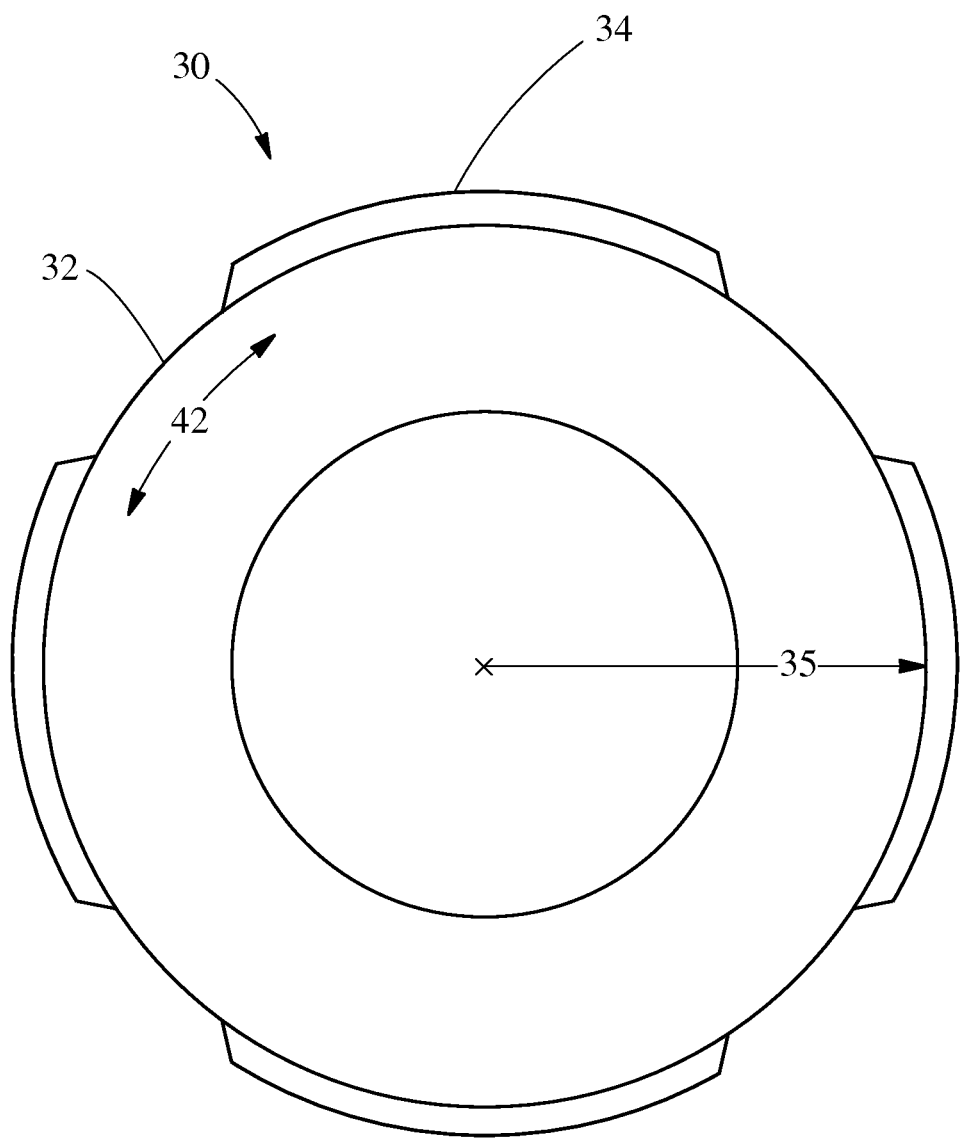
FIG. 4 is a side view of a rotary embossing device that can be used in the present invention.

With reference to FIGS. 1, 3 and 4, the embossing method for forming an absorbent article can include positioning an absorbent 22 core on a web material, such as a topsheet 24. Moving the topsheet 24 and absorbent core 22, either of which may be in the form of a continuous web or individual components as shown in FIG. 1, along a machine-direction 10 at a selected web speed, and in certain embodiments the topsheet 24 and absorbent core 22 may pass through two or more precalendering rolls 21. Precalendering may be used as the embossing step can require very high forces to achieve a stable bond. By precalendering, some of this compression can be done prior to the actual embossing step. Precalendering is not intended to do any permanent deformation of the absorbent core 22, but rather to partially compress targeted regions of the absorbent core 22 prior to embossing. This allows the embossing step to "complete" the bond in the embossed regions; the remaining areas of the absorbent core 22 are allowed to "rebound" from the Precalendering step. Following the precalendering rolls 21 (if used) the topsheet 24 and absorbent core 22 are operatively contacted with a rotary embossing device 30 to form an embossment region 40 in the body facing surface 23 and a depression region 41 in the garment facing surface 27 of the absorbent core 22.

Figure 4A:
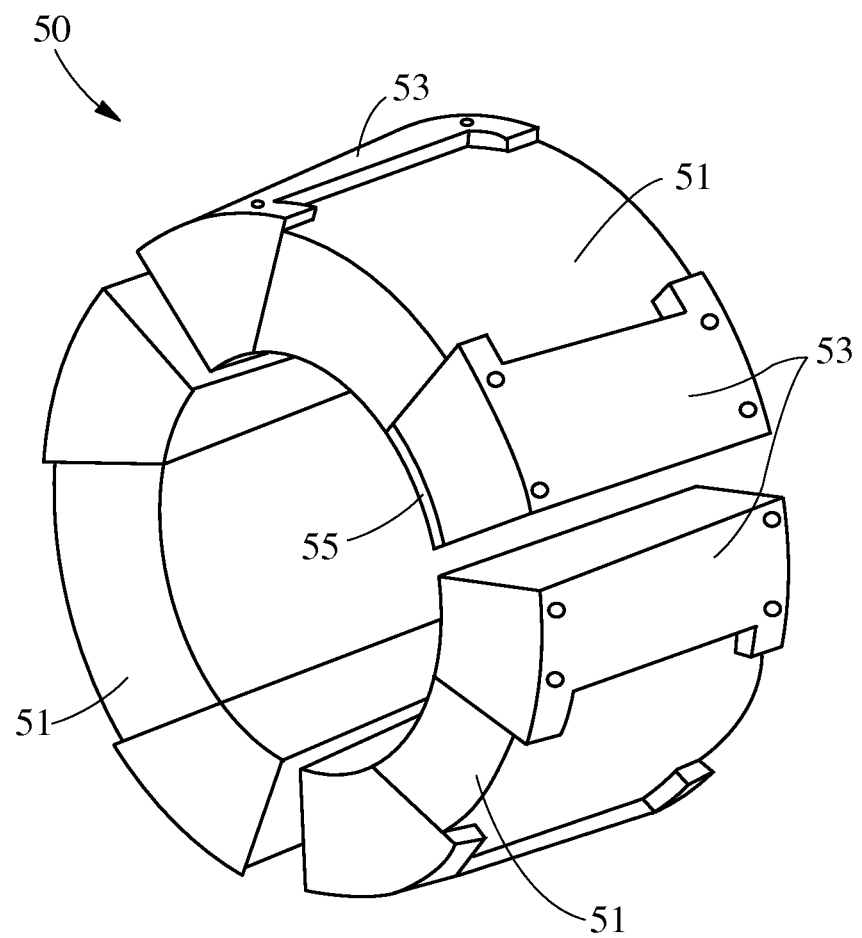
FIG. 4A is a perspective view of a segmented anvil member having segmented sections.

The rotary embossing device 30, as shown in FIG. 4, includes an outer peripheral surface 32 having a lateral cross-direction 12 and a circumferential-direction 42, and an embossing member 34 located on the outer surface 32. As shown in FIG. 1 the embossing method also includes a segmented anvil member 50 which has been configured to cooperate with the rotary embossing device 30. Additionally, the segmented anvil member 50 can be arranged to provide an operative embossing region which can be located between the rotary embossing device 30 and segmented anvil member 50. As shown in FIG. 4A the segmented anvil member 50 may include segmented sections 51. In certain embodiments, as explained in detail below, an embossing member 34 may have one or more closed ends as shown in FIG. 5, forming an embossment region 40 having a larger embossment in the cross-direction at the ends, which can reduce the depth of an embossment region 40. Current designs use an anvil member having a uniform diameter and an adjustable rotary embossing device. A segmented anvil member 50, as shown in FIG. 4A, having segmented sections 51 allows the more complex rotary embossing device to be machined at a uniform diameter, and moves the "adjustments" or variability to the simpler anvil member. Each segmented section 51 may have one or more movable portions 53, which in the embodiment shown in FIG. 4A are positioned at the end of each segmented section 51. The movable portions 53 can be elevated away from the segmented section 51 reducing the gap (between the rotary embossing 30 device and the segmented anvil member 50), using one or more elevation devices, such as a shim 55, at the end of the embossment member 34, thereby compensating for the reduction in pressure. In certain embodiments, the elevation device may be positioned between a movable portion and the mandrel to which the movable portion is engaged. In certain embodiments the elevation devices, such as a shim, may have a substantially constant thickness, which in certain embodiments may be from about 0.025 mm to about 0.25 mm. In certain embodiments the thickness of an elevated portion may vary. Further, movable portions may be separate elements from the segmented sections, and may be removed or fixed in place using means known in the art, such as by using nuts and bolts. In certain embodiments a segmented anvil member may have from 2 to 6 segmented sections, in certain embodiments a segmented anvil member may have from 3 to 9 segmented sections.

In certain embodiments, the absorbent core 22, if in web form, can be cut or otherwise divided to provide individual absorbent cores for use in feminine care articles, such as the feminine sanitary napkin shown in FIGS. 2 and 3. The feminine sanitary napkin 80 can have a lengthwise-dimension along the longitudinal direction 10, and a transverse-dimension along the laterally extending, cross-direction 12, which correspond respectively to the machine direction 10 and lateral cross-direction 12 described previously.

The absorbent core 22 is embossed before coming into contact with the backsheet. This allows the absorbent core 22 to be embossed to a greater depth in the embossed regions 40, while substantially avoiding undesired breaks or fractures of component portions of an absorbent article, such as a backsheet.

With reference to FIG. 1, the absorbent core 22 can be configured, for example by being positioned on a belt, to move at a selected speed in the machine-direction 10 of the method. In certain embodiments the speed can be from about 2 meters per second (m/s) to about 9 m/s, and in certain embodiments the speed can be from about 5 m/s to about 7 m/s.

FIGS. 2 and 3 show an absorbent article, which in this instance is a feminine sanitary napkin 80 having an absorbent core 22 positioned between a body facing surface 23 comprising a topsheet 24 and a garment facing surface 27 comprising a liquid impervious backsheet 28 joined to the topsheet 24, absorbent core 22, or both. The body facing surface 23 of the feminine sanitary napkin 80 has an embossment region 40 having a depth "D" as measured from the surrounding area of the body facing surface 23 to the lowermost portion of the embossment region 40. In certain embodiments the depth "D" of the embossment region 40 in the body facing surface 23 may be between about 20% to about 75% of the thickness "T" of the absorbent article, which in this instance is a feminine sanitary napkin, in certain other embodiments the depth "D" of the embossment region 40 may be between about 25% to about 50% of the thickness "T" of the absorbent article. The thickness of the absorbent article is measured at room temperature and at standard pressure and humidity. Embossment regions having this depth provide the benefit of improved body fit, good fluid barrier as well as aesthetic visual effects. The garment facing surface 27 of the feminine sanitary napkin 80 has a depression region 41 having a depth "$D_1$" as measured from the surrounding area of the body facing surface 27 to the lowermost portion of the depression region 41. In certain embodiments the depth "$D_1$" of the depression region 41 in the garment facing surface 27 may be between about 15% to about 75% of the thickness "T" of the absorbent article, which in this instance is a feminine sanitary napkin, in certain other embodiments the depth "$D_1$" of the depression region 41 may be between about 25% to about 50% of the thickness "T" of the absorbent article. While the garment facing surface 27 of the feminine sanitary napkin 80 is not directly contacted by the rotary embossing device 30, a depression region 41 is produced. While not being limited to theory it is thought that the depression region 41 in the garment facing surface 27 is formed from the tensioning of the topsheet, absorbent core and secondary topsheet (if present). Following embossment and the removal of the rotary embossing device and segmented anvil member the recovery of the materials forming the topsheet, absorbent core, and secondary topsheet draws or pulls the materials back up towards the center of the embossment region and body facing surface of the feminine sanitary napkin.

The feminine sanitary napkin 80 has a longitudinal axis "L" and may also be provided with additional features commonly found in feminine sanitary napkins, such as "wings" or "flaps" as is known in the art or a fluid acquisition layer to promote fluid transport to the absorbent core 22. Further, the topsheet of the absorbent article can have various optional characteristics, as is known in the art, for example the topsheet can have apertures to aid in fluid acquisition.

In certain embodiments the topsheet may be compliant, soft feeling, and non-irritating to the wearers skin and hair. Further, the topsheet is liquid pervious, permitting liquids, such as menses or urine, to readily penetrate through its thickness. A suitable topsheet may be manufactured from a wide range of materials such as woven and nonwoven materials, for example a nonwoven web of fibers; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of: natural fibers, such as wood or cotton fibers; synthetic fibers, such as polymeric fibers—for example polyester, polypropylene, or polyethylene fibers; or from a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like.

The backsheet is substantially impervious to liquids, such as menses or urine and may be manufactured from a thin plastic film, although other flexible liquid impervious materials may also be used. The backsheet prevents the exudates absorbed by the absorbent core from wetting a user's bedding or clothes, for example bedsheets, pants, pajamas and undergarments. In certain embodiments, the backsheet can operatively permit a sufficient passage of air and moisture vapor out of an absorbent article, particularly out of the absorbent core, while blocking the passage of bodily liquids. The backsheet may thus comprise: a woven or nonwoven material; polymeric films, such as thermoplastic films of polyethylene or polypropylene; or composite materials such as a film-coated nonwoven material. In one embodiment, the backsheet can be a breathable backsheet such as that described in U.S. Pat. No. 6,623,464 (Bewick-Sonntag et al.) issued 23 Sep. 2003.

As shown in FIG. 3 the backsheet 28 and the topsheet 24 are positioned at the garment facing surface 27 and the body facing surface 23, respectively, of the feminine sanitary napkin 80. In certain embodiments the absorbent core can be joined with the topsheet, the backsheet, or both by known attachment means, such as those well known in the art. However, in certain embodiments of the present invention the absorbent core is unattached to the topsheet, the backsheet, or both.

The absorbent core 22 in FIGS. 2 and 3 is generally disposed between the topsheet 24 and the backsheet 28. The absorbent core 22 may comprise any absorbent material that is generally compressible, conformable, non-irritating to the wearer's skin, and capable of absorbing and retaining liquids such as urine and other certain body exudates, such as menses. The absorbent core 22 may comprise a wide variety of liquid-absorbent materials commonly used in feminine care articles and other absorbent articles, such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates; absorbent foams such as foams formed from High Internal Phase Emulsions (HIPEs); absorbent sponges; superabsorbent polymers; absorbent gelling materials; or any other known absorbent material or combinations of materials. The absorbent core may further comprise minor amounts (typically less than 10%) of non-liquid absorbent materials, such as adhesives, waxes, oils and the like. Examples of absorbent structures that may be used in the present invention are found in U.S. Pat. No. 4,834,735 (Alemany et al.) issued 30 May 1989; U.S. Pat. No. 5,625,222 (DesMarais et al.) 22 Jul. 1997.

The absorbent core may also include one or more superabsorbent materials. Superabsorbent materials suitable for use in the present invention are known to those skilled in the art, and may be in any operative form, such as particulate form. The superabsorbent material can be a water-swellable, generally water-insoluble, hydrogel-forming polymeric absorbent material, which is capable of absorbing at least about 20, in certain embodiments about 30, and in additional embodiments about 60 times or more its weight in physiological saline (for example 0.9 wt % NaCl). The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers are preferably lightly crosslinked to render the material substantially water insoluble. Crosslinking may, for example, be by irradiation or covalent, ionic, Van der Waals, or hydrogen bonding. Suitable materials are available from various commercial vendors, such as the Dow Chemical Company and Stockhausen, Inc. The superabsorbent material may be included in an appointed storage or retention portion of the absorbent article, and may optionally be employed in other components or portions of the absorbent article.

As shown in FIG. 1, the rotary embossing device 30 can be positioned cooperatively adjacent a segmented anvil member 50. The segmented anvil member 50 is oriented to counterrotate relative to the rotary embossing device 30.

The rotary embossing 30 device can have a selected roll radius 35. In certain embodiments the roll radius can be from about 7 cm to about 25 cm. In certain other embodiments the roll radius can be from about 11 cm to about 19 cm.

Any conventional power mechanism or system can be employed to drive the rotary embossing device 30. Such power mechanisms can include engines, motors, electromagnetic power systems, fluidic power systems, or the like, as well as combinations thereof The selected drive system can be configured to provide the rotary embossing device 30 with a selected surface speed at the outer peripheral rim surface 32, and certain embodiments, the peripheral surface speed can be configured to substantially equal the web speed of the absorbent core that is to be embossed.

As shown in FIG. 4 the rotary embossing device 30 can have an outer peripheral rim surface 32 which extends along the circumferential direction 42 and along the transverse cross-direction 12 of the rotary embossing device. With reference to FIGS. 1, 4, 5 and 6, at least one embossing member 34 can be located on the outer peripheral surface 32 of the rotary embossing device 30. In certain embodiments a plurality of two or more embossing members 34 can be distributed over the outer peripheral surface 32 in a desired array. For example, the plurality of embossing members can be arranged in series along the circumferential direction of the embossing device 30, and the serial arrangement may be irregular or substantially regular, as desired.

While the embossing member 34 can be of any desired shape, design or combination of shapes and designs for providing the desired embossment to an absorbent article an embossing member 34 in certain embodiments, as shown in FIG. 5 may comprise a primary shape 38 bordered by two or more secondary shapes 39.

An embossing member may provide to an absorbent article a symmetrical shape, an asymmetrical shape, a regular or irregular rectilinear shape, a regular or irregular curvilinear shape or the like, as well as combinations thereof. The embossing member may be configured to be discontinuous or substantially continuous, as desired. In particular arrangements, the embossing member can be arranged to effectively provide a substantially closed-shape. In certain embodiments the embossing member can be configured to extend along substantially an entirety of the absorbent core perimeter during the embossing operation.

Figure 6:
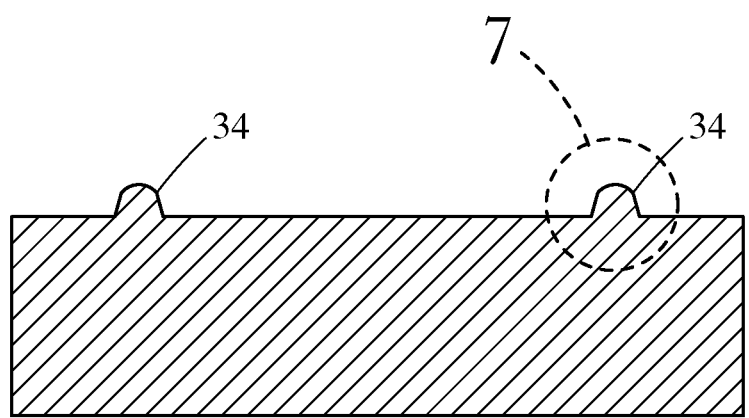
FIG. 6 is a view of a cross-section of the embossment member of FIG. 5 along the cross-directional line 6-6.
Figure 7:
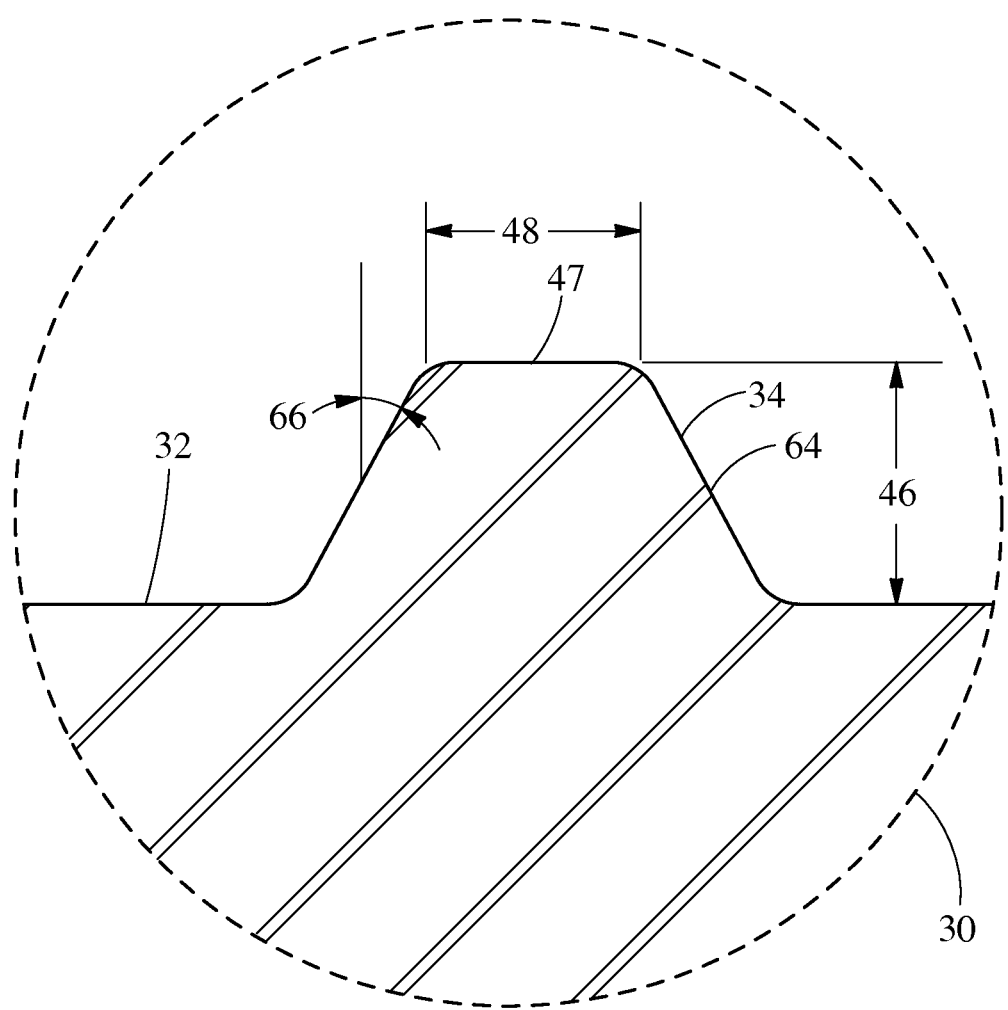
FIG. 7 is an enlarged view of a cross-section through a portion of an embossing member.

With reference to FIGS. 6 and 7, an embossing member 34 can have an embossing member height 46 and an embossing member width 48. The embossing member height 46 is the distance between the topmost portion of the embossing member surface 47 and a corresponding local outer-surface region 32 of the embossing device. In certain embodiments, the embossing member height 46 can be from about 2 mm to about 12 mm. In certain other embodiments the embossing member height 46 can be from about 3 mm to about 4 mm. With reference to FIG. 7, in certain embodiments the embossing member width 48 can be from about 0.25 mm to about 4 mm. In certain embodiments the embossing member width 48 can be from about 0.5 mm to about 2 mm. The embossing member 34 can include sidewall regions 64, and the sidewall regions can have a sidewall angle 66. In certain embodiments the sidewall angle can be from about 0 degrees to about 50 degrees. In certain other embodiments the sidewall angle can be from about 10 degrees to about 20 degrees.

Figure 8:
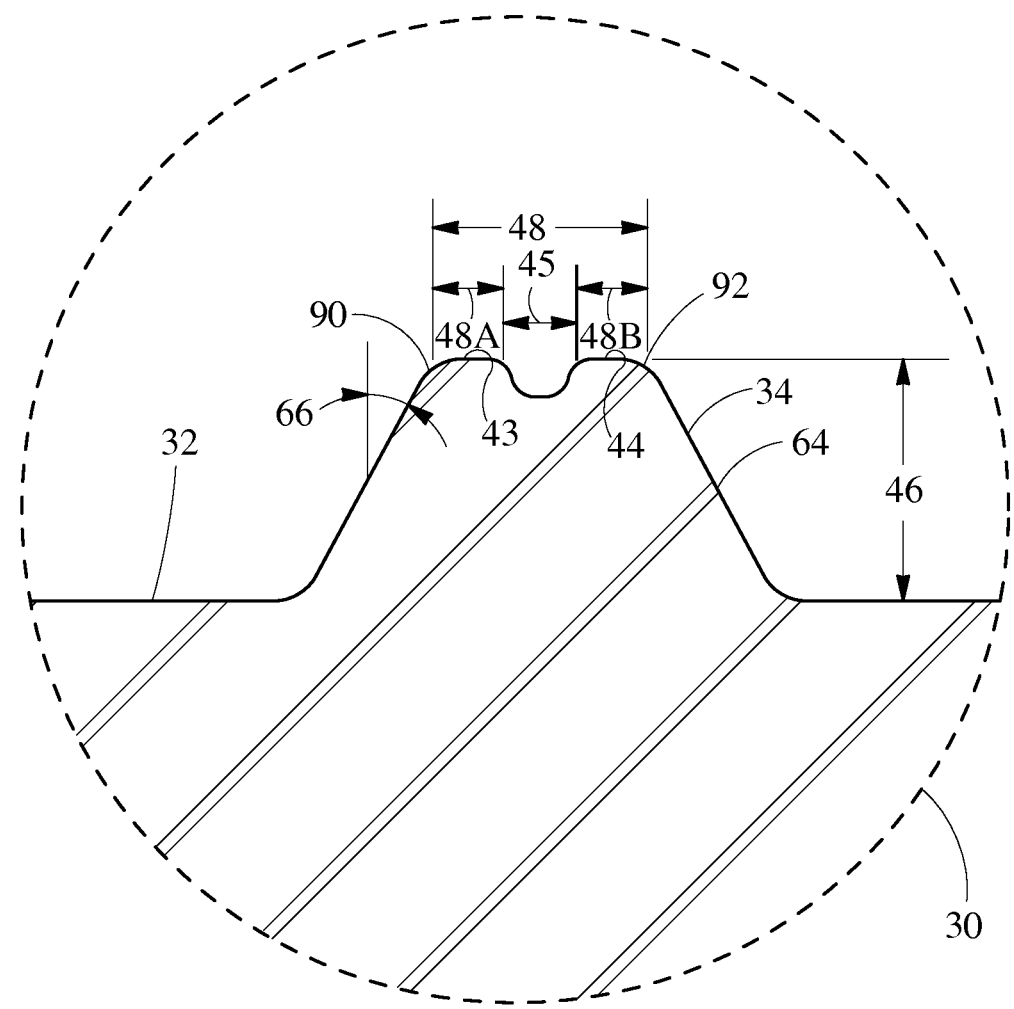
FIG. 8 is an enlarged view of a cross-section through a portion of an embossing member.

As shown in FIG. 8, in certain embodiments the embossing member 34 can include a plurality of two or more embossing-elements 43, 44. For example, as shown, the embossing member 34 can include a first embossing-element 43 and a second embossing-element 44, which is located adjacent the first embossing-element 43. There can be a selected separation distance 45 between the immediately adjacent embossing-elements 43, 44. In certain embodiments, a separation distance between a first 43 and second embossing-element 44 may be from about 0.05 cm to about 0.8 cm. In certain other embodiments, a separation distance between a first 43 and second embossing element 44 may be from about 0.1 cm to about 0.4 cm. The multi-element embossing member 34 can have an overall width 48, as measured between an outward-edge 90 of first embossing-element 43 and an outward edge 92 of the second embossing-element 44. In certain embodiments the embossing member width 48 can be from about 0.15 cm to about 2.2 cm. In certain other embodiments the embossing member width 48 can be from about 0.3 cm to about 1 cm. The first embossing-element 43 can have a first embossing element width 48A and the second embossing-element 44 can have a second embossing-element width 48B. In certain embodiments the first embossing element or second embossing element width 48A, 48B can be from about 0.25 mm to about 4 mm. In certain embodiments the first embossing element or second embossing element width 48A, 48B can be from about 0.5 mm to about 2 mm.

In another aspect of the method, the contacting of the topsheet 24 and absorbent core 22 with an embossing member 34 of the rotary embossing device 30 can be configured to apply a selected embossing force value to an embossing region. In certain embodiments the embossing force value can be from about $1\times10^5$ Newtons per meter (N/m) to about $3\times10^7$ N/m across the width of the embossing region, for example as found in the nip region between the rotary embossing device 30 and the rotary segmented anvil member 50. In certain embodiments the embossing force value can be from about $5\times10^6$ N/m to about $2\times10^7$ N/m across the width of the embossing region, for example as found in the nip region between the rotary embossing device 30 and the rotary segmented anvil member 50.

With reference to FIG. 1 the method can include attaching a backsheet 28 to the topsheet 24, absorbent core 22 or both.

In certain embodiments the backsheet 28 may be attached to the topsheet 24, absorbent core 22, or both after contacting the absorbent core 22 with the rotary embossing device 30. As shown in FIG. 3 portions of the backsheet 28 will conform to the contours of the depression regions 41, thereby creating an irregular surface. The various portions or components of each absorbent article, such as the absorbent core 22, topsheet 24 or backsheet 28 can be joined or secured together employing any operative technique. A variety of suitable mechanisms known to one of skill in the art may be utilized to achieve any such secured relation. Examples of such securing mechanisms or systems can include, but are not limited to, the application of adhesives in a variety of patterns between the two adjoining surfaces, entangling at least some portions of one absorbent body component with portions of the adjacent surface of another component, or fusing at least portions of the adjacent surface of one component to portions of another component of the absorbent.

Referring back to FIG. 1, following its attachment a backsheet 28 is contacted by one or more streams of adhesive, which may be in the form of meltblown adhesive, spray coating resins, or web forming resins. As is conventionally known, the term "meltblown" is generally descriptive of a process used to form a random network of entangled heat-fusible fibers. In operation, a low viscosity, molten polymer is extruded through a series of small discharge orifices formed in the extruder die to define a series of continuous fibers. These fibers are immediately exposed to a heated, high velocity airstream for disrupting or attenuating the flow of molten polymer. Due to the flow disruption caused by such air impingement, the meltblown fibers are formed into a random, entangled network of heat-fused fibers upon deposition on a continuously moving backsheet. Thus, the resulting series of fibers are typically continuous filaments or have one or more discrete lengths, and a fiber diameter, which in certain embodiments may be in the range of from about 5 microns to about 120 microns, and in certain other embodiments from about 7 microns to about 30 microns. The resulting meltblown adhesive layer may include a plurality of such fibers distributed in sufficient amount to achieve the desired peel force of between about 70 grams of force (go to about 500 gf. The fibers may be distributed generally in a random manner, in a non-woven manner, or in a generally sine-wave like manner to produce an adhesive layer.

A meltblown adhesive may include one or more polymers, such as (1) cohesive strength modifiers to increase the cohesive strength, for example aliphatic polyolefins such as ethylene-propylene copolymers, polyetheramides, polyetheresters; ethylene vinyl acetate copolymers; styrene-butadiene or styrene-isoprene block copolymers; resins or analogous material (sometimes called a tackifier); (2) adhesive strength modifiers to increase the adhesive strength, for example hydrocarbons distilled from petroleum distillates; rosins or rosin esters; terpenes derived, for example, from wood or citrus; (3) viscosity modifiers to increase or decrease the viscosity of a meltblown adhesive, such as waxes, plasticizers, mineral oil, polybutene, paraffin oils, ester oils, and the like. A meltblown adhesive may also include other additives including, but not limited to, antioxidants or other stabilizers.

Various plasticizing or processing oils may also be present in the meltblown adhesive compositions of the present invention in amounts ranging from about 0% to about 30%, by weight of the overall adhesive composition, in order to aid in providing viscosity control, and further to operate as a diluent. Paraffinic or napthenic white processing oils may be used. Antioxidants or stabilizers may also be used in suitable amounts in the adhesive composition to help protect adhesives from potentially deleterious thermal and oxidative effects, which may take place during the manufacture and application of adhesives. Such degradation, if it occurs, usually causes deterioration of the adhesive composition in appearance, physical properties and performance. Examples of suitable stabilizers include one or more of high molecular weight hindered phenols and multi-functional phenols, such as sulfur and phosphorous-containing phenols.

In certain embodiments, meltblown adhesives may have a melt temperature of between about 135° C. to about 260° C., a viscosity of less than about 200,000 centipoises (cps) at about 165° C., and an application viscosity (viscosity at about the time it is meltblown) in the range of about 10,000 cps to about 50,000 cps, and in certain other embodiments in the range of about 20,000 cps to about 35,000 cps. Further, in certain embodiments, the meltblown adhesive may have a density of from about 0.8 g/cm$^3$ to about 1.2 g/cm$^3$. Since the adhesive may be meltblown, the meltblown adhesive can be capable of resulting in a forming distance (the distance between a discharge nozzle orifice and a substrate to which the material is applied) of from about 8 mm to about 25.4 mm with a resulting drop of temperature along the length of formed filaments of about 10° C.

The adhesive may also exhibit good forming edge definition (consistency of the adhesive pattern width during filament formation), for example an edge definition variation in certain embodiments from 0 mm to about 4 mm, and in certain embodiments of from 0 mm to about 2 mm, of the desired pattern width, when forming within a forming distance of about 8 mm to about 25.4 mm. The adhesive pattern also has a defined surface area. The defined surface area of an adhesive pattern is the surface area on the substrate having at least one depression region, such as a backsheet, upon which the adhesive pattern is to be applied. In certain embodiments the adhesive covers at least 95% of the adhesive pattern defined surface area; in certain other embodiments the adhesive covers at least 90% of the adhesive pattern defined surface area; in still further embodiments the adhesive covers at least 80% of the adhesive pattern defined surface area. In certain embodiments the adhesive may be applied in an amount of from about 13 grams per square meter (gsm) to about 19 gsm. Further less than 5% of the adhesive within the adhesive pattern defined surface area forms strings of adhesive upon removal of the release paper. Wherein strings of adhesive are observable by the naked eye of the observer having 20/20 vision from a distance of about 30 cm; and are formed when adhesive remains attached to both the release paper and substrate to which the adhesive has been applied, upon removal of the release paper—causing the adhesive to stretch and form strings. In certain embodiments, less than 2% of the adhesive within the adhesive pattern defined surface area forms strings.

Figure 9:
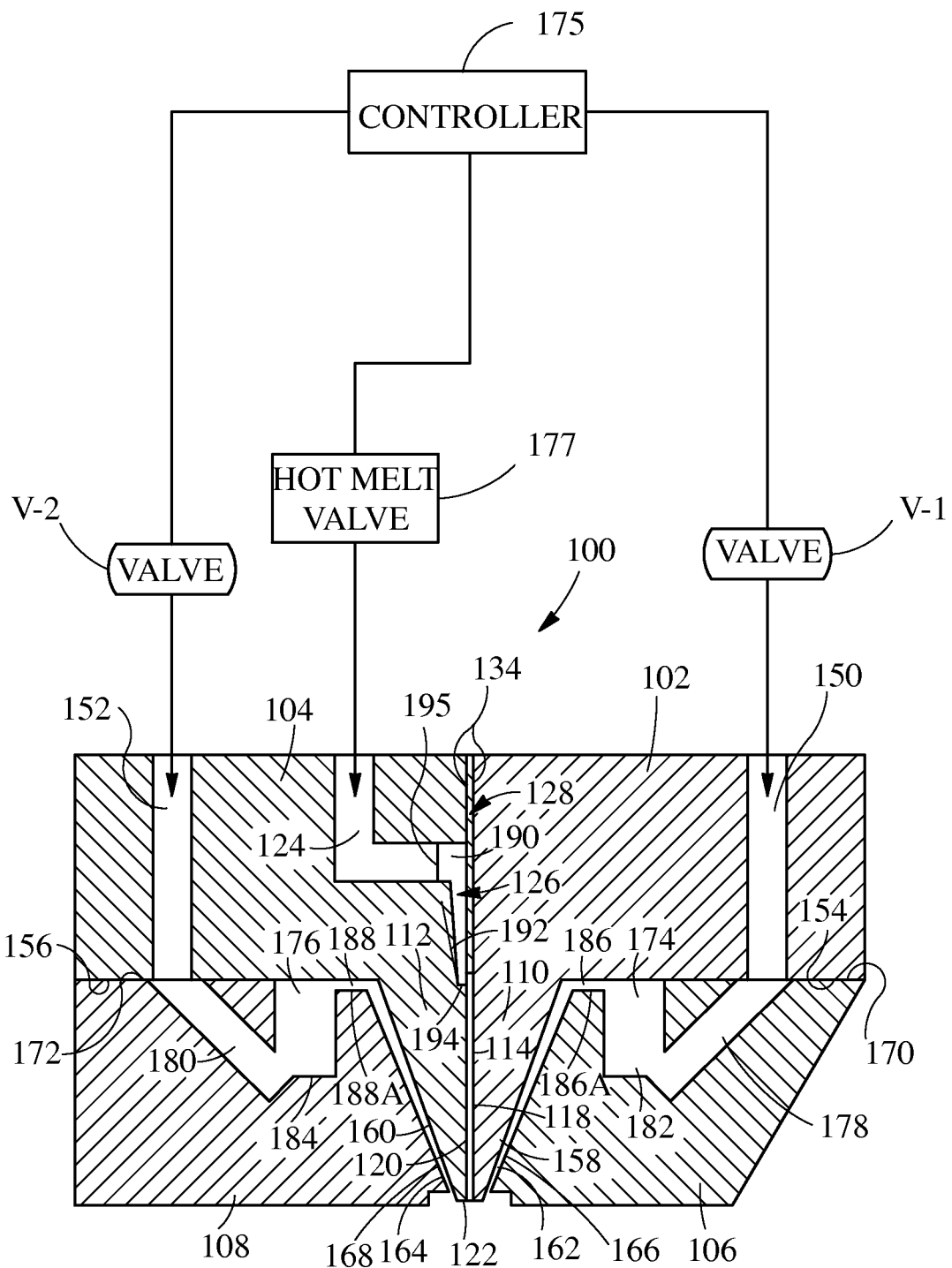
FIG. 9 is a diagrammatic side view in partial cross-section of a non-contact die means that can be used in the present invention.

FIG. 9 illustrates an example of a non-contact die means 100 that may be used in the present invention. The die means 100 comprises two die halves, a first die half 102 and a second die half 104, and two air blocks 106, 108. Each die half 102, 104 includes a downwardly depending projection 110, 112. The die halves 102, 104 define between them an extrusion slot 114. The extrusion slot 114 is defined by the face 118 of the first die half 102 and the face 120 of the second die half 104. Face 118 is juxtaposed with respect to the face 120, as shown in FIG. 9. The extrusion slot 114 terminates at an elongated slot or extrusion outlet 122.

Figure 10:
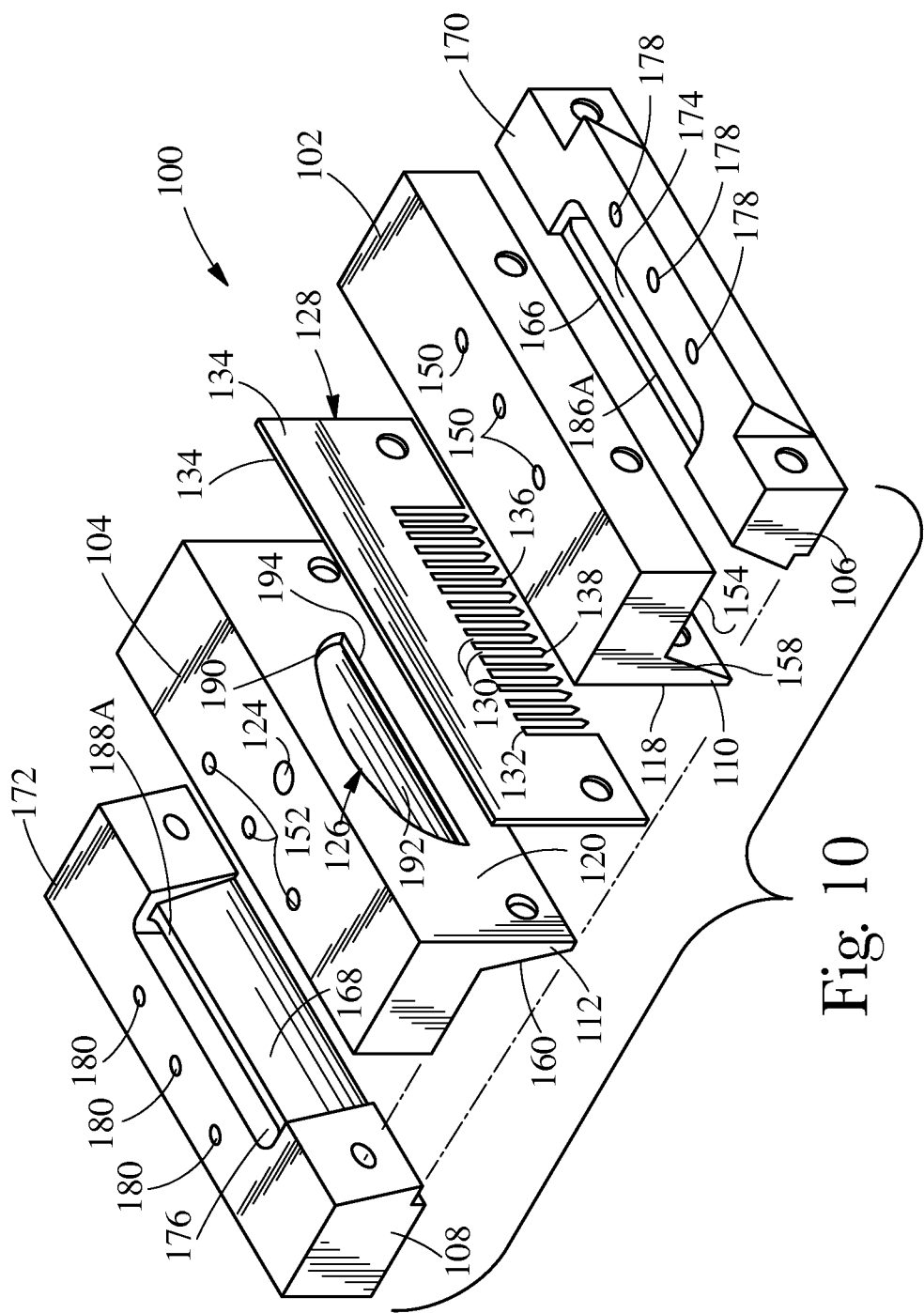
FIG. 10 is an exploded view of the non-contact die means shown in FIG. 9.
Figure 12:
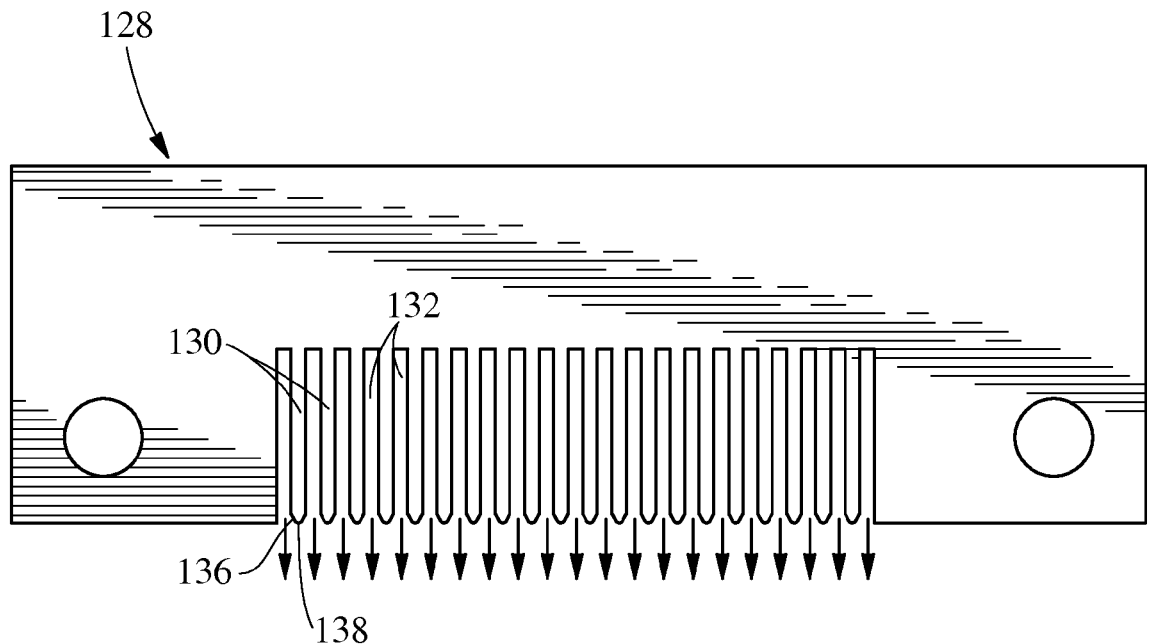
FIG. 12 is a front view of a slotted shim that can be used in a non-contact die means.

The second die half 104 includes a hot melt passageway 124 for receiving hot melt adhesive and conducting the hot melt adhesive to a "coat hanger" portion 126 of the second die half 104, which may be better seen in FIG. 10. A slotted or segmented shim 128, as best seen in FIG. 12, and a portion of which is seen in FIG. 9, is located between the juxtaposed surfaces 118, 120 of the die halves 102, 104. The shim 128 has a plurality of elongated projections 130, extending towards the extrusion outlet 122, defining between them a plurality of elongated channels or slots 132. In FIG. 9, only the top portion 134 of the shim 128 is shown, for the purpose of clarity.

Figure 13:
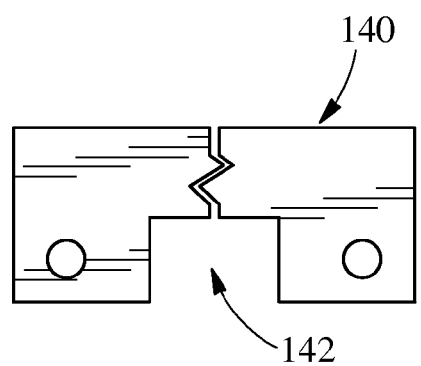
FIG. 13 is a front view of a slotted shim that can be used in a non-contact die means.

Once again with reference to FIG. 12, each of the projections 130 has a downstream tapered end portion 136, having a tip 138. In certain embodiments, an open shim can be used. An example of an open shim 140 is depicted in FIG. 13. This shim 140 has an open area 142, with no projections 130, as seen in FIG. 12. Also, in another embodiment, the tapered end portion 136 or tips 138 can extend beyond outlet 122.

Returning to FIG. 9, each of the die halves 102, 104 is provided with a primary air passageway 150, 152, extending from an upper surface of the die to a lower respective surface 154, 156. Each die half 102, 104 also includes an inclined surface 158, 160, depending from the surfaces 154 and 156, respectively. The inclined surfaces 158, 160 define one part of an air elongated slot 162, 164, as will be described in more detail below.

Positioned below the die halves 102, 104 are the air blocks 106, 108, each of which include an inclined surface 166, 168 that defines the other side of the air slots 162, 164 with the juxtaposed respective surfaces 158, 160, as shown in FIG. 9. Each of the air blocks 106, 108 include an upper surface 170, 172 juxtaposed to the respective lower surfaces 154, 156 of the die halves 102, 104.

An elongated air plenum 174, 176 is formed in each of the air blocks 106, 108. The plenums 174, 176 are also shown in FIG. 10. Respective secondary air passages 178, 180 are formed in the respective air blocks 106, 108 and extend from the respective surfaces 170, 172 to a lower portion 182, 184 of the respective plenums 174, 176. Each of the plenums 174, 176 are primarily defined in the air blocks 106, 108. However, the top areas of each of the respective plenums 174, 176 are also defined respectively by the lower surfaces 154, 156 of the die halves 102, 104. The lower surfaces 154, 156 also form an upper portion of tertiary air passages 186, 188, each of which respectively lead from their associated plenums 174, 176 to the air slots 162, 164. Accordingly, as shown in FIG. 9 air can pass through the primary passageway 150 to the secondary passageway 178 in air block 106, and from there to the plenum 174. From the plenum 174, pressurized air moves through the tertiary passageway 186 into the air slot 162 of the air block 106.

In a like manner, air can be introduced to primary passageway 152 in the die half 104 and from there it can move into the secondary air passageway 180 and into the lower portion of the plenum 176. From the plenum 176, pressurized air is directed through the tertiary air passage 188 into the air slot 164 of the air block 108.

As shown in FIG. 9, in certain embodiments, a controller 175 is operationally connected to valves V-1 and V-2, for controlling the introduction of heated, pressurized air to the primary passages 150, 152, respectively, in order to pressurize those passages and the downstream air passages with air, as previously described. At the same time, the controller 175 is operationally interconnected to a hot melt control valve 177 for controlling the supply of coating material, such as hot melt adhesive, to the hot melt adhesive passage 124 and to the internal coat hanger area 126 of the die means 100. Any suitable form of controller 175 can be used. A controller 175 can initiate and stop the generation of air into primary passages 150, 152, either simultaneously or independently, and can also initiate and stop the hot melt flowing through valve 177 so as to intermittently provide coating material to the passageway 124, independently and at pre-selected times with respect to the supply of pressurized heated air to the primary passages 150, 152, as described in more detail below.

The air slots 162, 164 are oriented on an angle with respect to the length of the extrusion slot 114. Accordingly, when coating material is extruded through the extrusion slot 114 and outwardly of the extrusion outlet 122, air moving through the air slots 162, 164 is impinged on the material before that material engages or is deposited on an underlying substrate which is presented for coating.

Any suitable apparatus can be utilized for melting and pumping hot melt adhesive to the hot melt control valve 177.

Referring to FIG. 9 and the details of the die means 100 as shown in FIG. 10, it will be appreciated that the plenums 174, 176 in the air blocks 106, 108 communicate with the lower surfaces 186A, 188A, respectively, of the tertiary air passages 186, 188 as previously described, and air emanating from the upper portion of the plenums 174, 176 moves through the tertiary passageways 186, 188, and then downwardly through the respective air slots 162, 164.

The die means 100, as shown in FIG. 10, incorporates a "coat hanger" portion 126 having an arcuate slot 190 of increasingly shallow dimension communicating with an incline surface 192. Surface 192 is inclined such that its lower portion, where it meets bottom surface 194, is closer to the plane of the face 120 than is the upper portion. It will also be appreciated that slot 190 is of decreasing depth as its distance from port 195 continues until it flows unbroken in surface 192. The arcuate slot 190 of decreasing depth is fed by the hot melt port 195, which is interconnected to the hot melt passage 124. In use, when hot melt adhesive is supplied at pressure to the passage 124, it exudes through the port 195 into the arcuate slot 190 and from there flows over the surface 192 and spreads out throughout the coat hanger shaped portion 126 of the die face 120 and the side of the shim 128 which is juxtaposed to the face 120 of the die half 104.

The slots 132 of the shim 128 have upper ends which communicate with the lower portion of the coat hanger die area 126, just above the surface 194 thereof, so that hot melt adhesive can flow into the slots 132 and then downwardly to the extrusion outlet 122. In this manner, the hot melt adhesive is spread throughout the coat hanger portion 126 and across each of the upper ends of the slots 132 of the shim 128 at significantly equal pressures, so that hot melt adhesive can move through the extrusion slot 114 within the slots 132 of the shim 128 at relatively equal pressures.

As illustrated diagrammatically in FIG. 12, the material exudes through the slots 132 and then outwardly of the extrusion outlet 122.

In certain embodiments, the width of a slot 132 between the projections 130 may be about twice the thickness of the shim 128. The thickness of one shim 128 may be about 0.1 mm while the slot width—that is the distance from one projection 130 across to the next projection 130, may be about 0.2 mm. In another shim 128, for example, the shim thickness may be about 0.2 mm while the segmented slot width between juxtaposed projections may be about 0.4 mm.

While the ratio of the shim thickness to the shim slot width may be about 2 to 1, this ratio can be varied to produce varying hot melt adhesive thicknesses. The width and thickness parameters of the shims 128, 140 and their components can vary. The parameters may vary due to the basis weight of hot melt adhesive per square meter desired, the cohesiveness desired, the hot melt adhesive viscosity or other factors.

For the application of hot melt adhesive to an absorbent article, the die means 100 impinges hot air from the air slots 162, 164 on each side of the hot melt adhesive exuding from the extrusion outlet 122. The impinging air engages and shreds the hot melt adhesive into discrete micro-denier fibers. Edge control is uniform and the density of the pattern can range from 25% open or fibrous to 0% open, for example a non-porous film. The parameters are selected depending on the application to which the hot melt adhesives are to be applied.

In certain embodiments the die means 100 can selectively apply air flow through either air slot 162 or 164 individually or together during the deposition period, particularly to more accurately define the initial and ending contact position of the deposited coating on the substrate. One such mode of operation is illustrated in FIG. 11, where the apparatus is utilized, for example, to apply a hot melt adhesive to the backsheet of feminine sanitary napkin so that a release paper can be operatively attached thereto.

Figure 11:
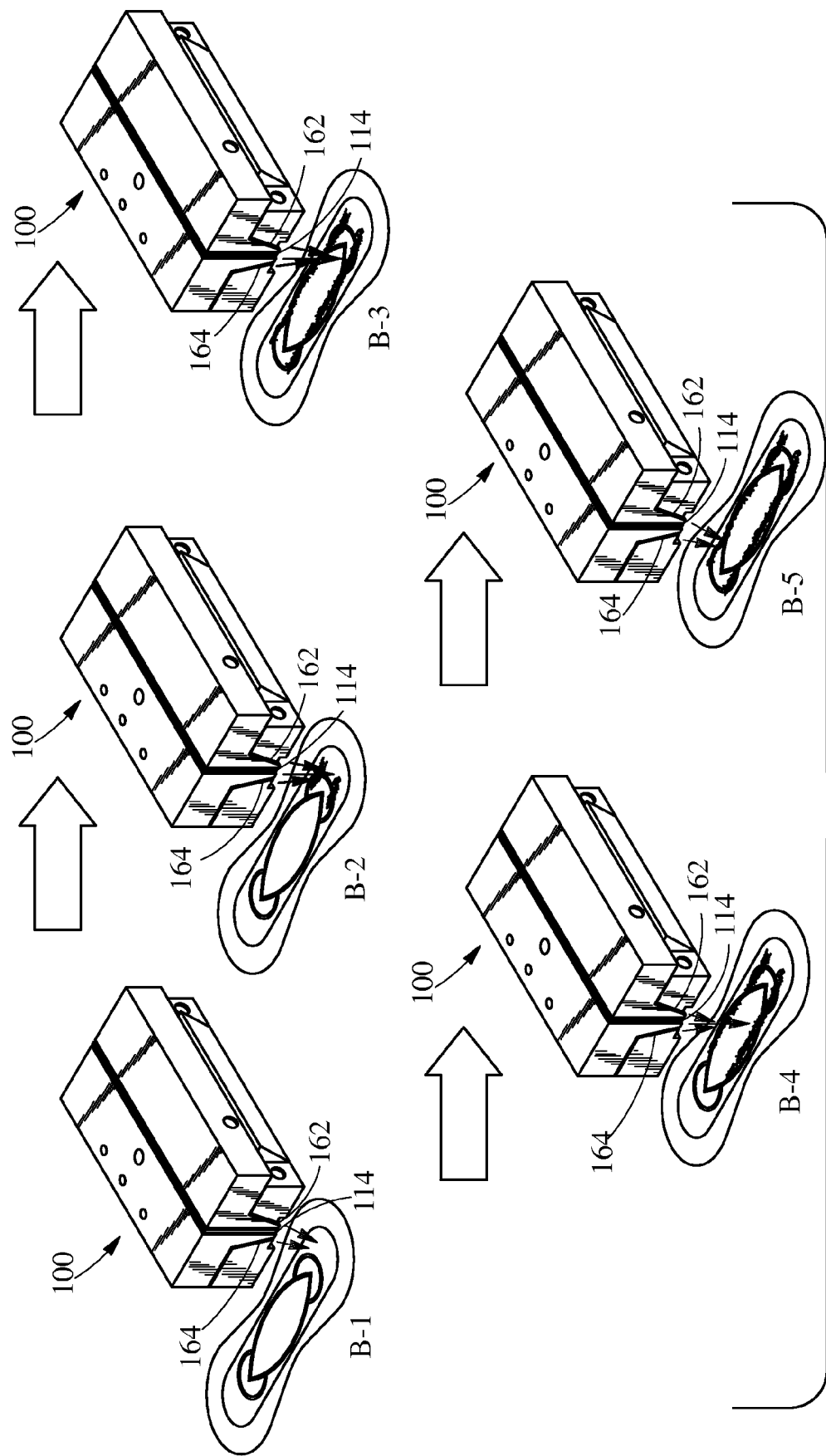
FIG. 11 is a diagrammatic view illustrating use of one embodiment of the present invention in an adhesive application to a feminine sanitary napkin.

In FIG. 11, a feminine sanitary napkin with no adhesive thereon is shown at the left hand side of the figure at position B-1. As illustrated at B-1, air flow has been initiated through the air slots 162, 164 but there is no hot melt adhesive being extruded through the extrusion slot 114. Moving to the feminine sanitary napkin at the position B-2, it will be appreciated that the hot melt flow adhesive has started and that it is impinged by air flowing through the air slots 162, 164. Since the air flowing through the air slots 162, 164 at position B3 and B4 moves downwardly in a general right to left direction as shown in FIG. 11, it will be appreciated that the hot melt adhesive does not string down the side of the feminine sanitary napkin but is applied directly to the backsheet of the feminine sanitary napkin with no stringing. Then, as shown in position B-5, the hot melt adhesive flow has ceased, while the air flowing through the air slots 162, 164 continues. This operation, when used in operatively attaching release paper to the backsheet of a feminine sanitary napkin, for example, would ensure that the adhesive will not string down the edges of the feminine sanitary napkin.

Accordingly, with respect to FIG. 11, the air flow is started before the extrusion of the hot melt adhesive and stopped after the hot melt adhesive extrusion has ceased. In this way, the air angling onto the hot melt adhesive does not blow it in strings over the edges of the feminine sanitary napkin, as that would be undesirable and yet the cut-off and cut-on edges of the hot melt adhesive are maintained in sharp, square fashion on the backsheet of the feminine sanitary napkin.

Figure 14:
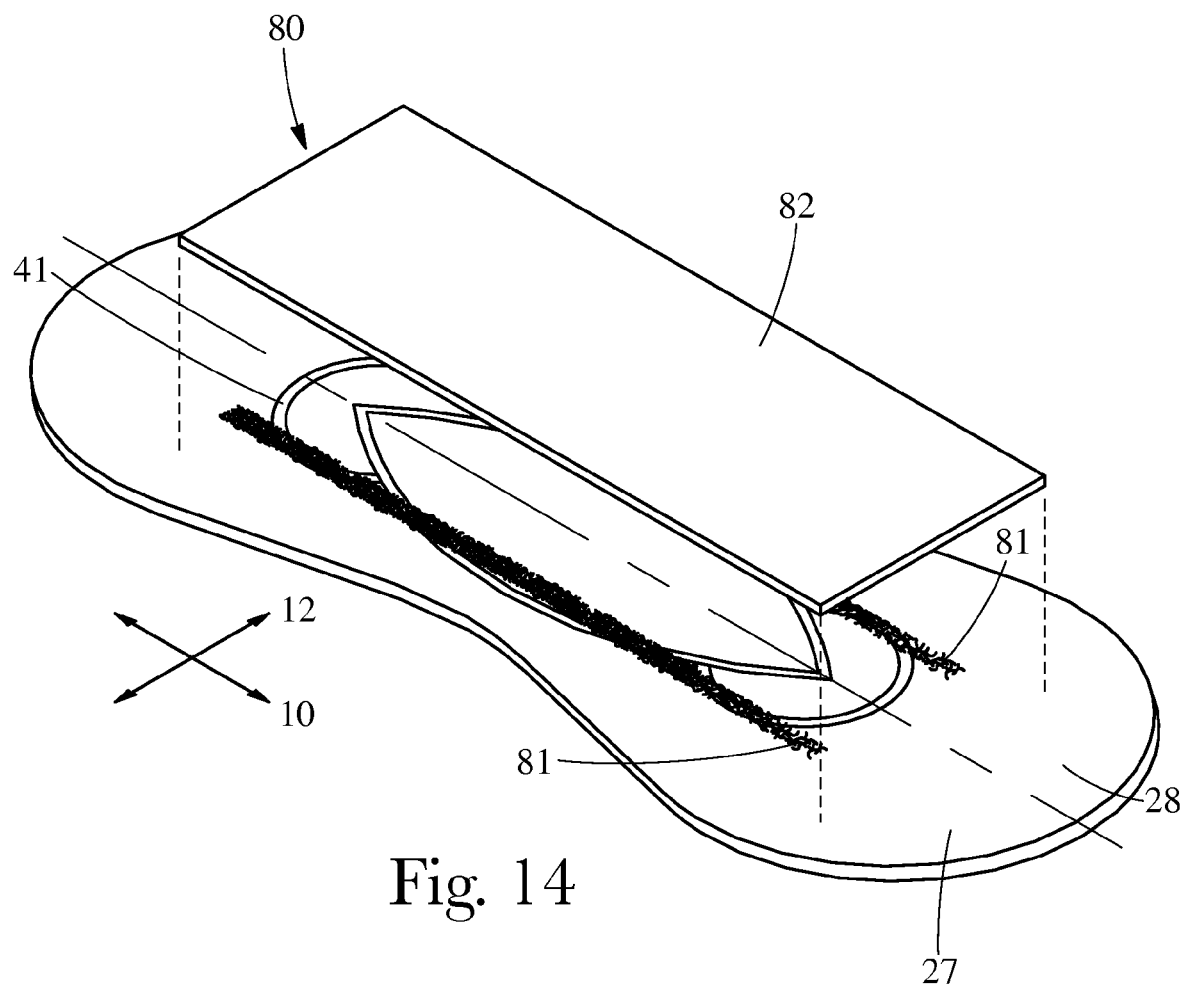
FIG. 14 is a perspective exploded view of a feminine sanitary napkin having adhesive thereon and a release paper.
Figure 15:
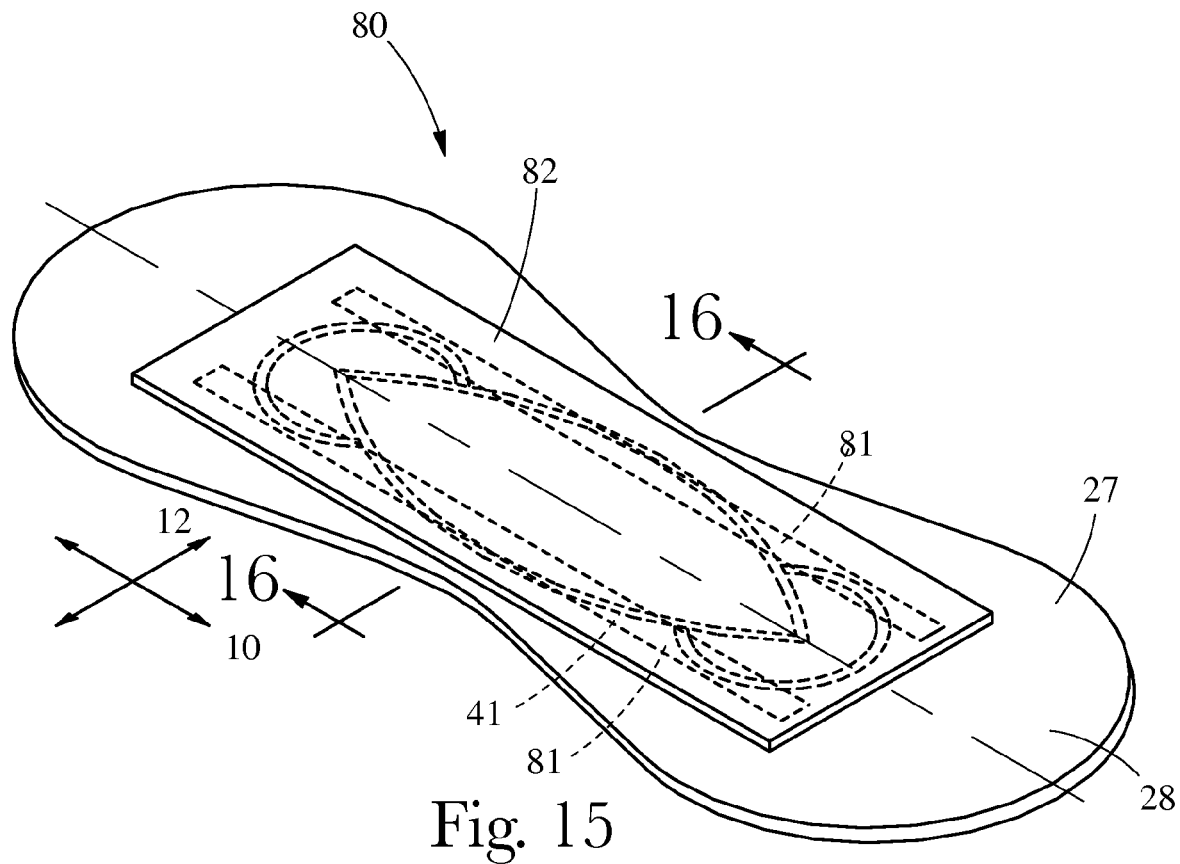
FIG. 15 is a perspective view of a feminine sanitary napkin having an attached release paper.
Figure 16:
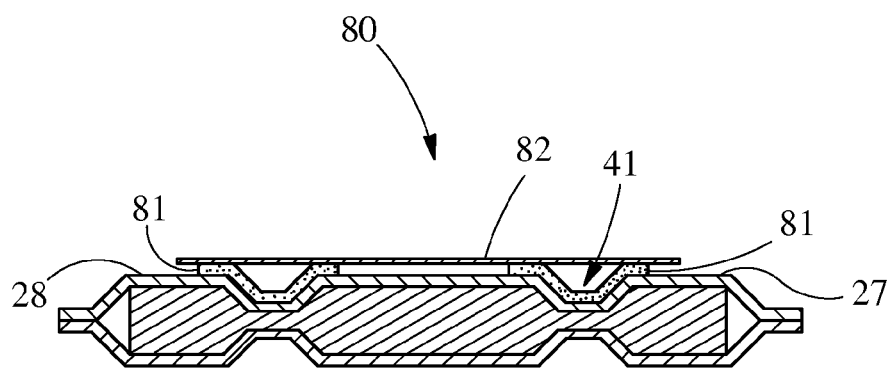
FIG. 16 is a view of a cross-section of the feminine sanitary napkin of FIG. 15 along the cross-directional line 16-16.

In FIGS. 14-16, a feminine sanitary napkin 80 is illustrated, such that the garment facing surface 27 is visible and the backsheet 28 and depression region 41 can be seen. An adhesive pattern 81 having a defined surface area that may be comprised of lines or bands of adhesive is applied by the apparatus described herein, in either fibrous or impervious form, to the backsheet 28 to releasably operatively attach the release paper 82. There can be more than one adhesive pattern per individual backsheet, for example an individual backsheet may have 2, 3, 4 or more individual adhesive patterns. Further the adhesive patterns may be in any suitable shape, for example rectangles, squares, crisscross patterns, asymmetric or symmetric shapes, and so on. As shown in FIG. 16 the adhesive pattern 81 present in both the substantially flat portions of the backsheet 28 and the portions of the backsheet 28 that conform to the depression region 41. The non-contact application of the adhesive allows the adhesive to adhere to the substantially flat portions of the backsheet 28 and the depression regions 41 providing increased adhesive coverage within the defined surface area of the adhesive pattern 81; as compared to contact methods of adhesive application, as described below. FIGS. 14-16 illustrate the adhesive patterns 81 may vary in width. The adhesive patterns can be applied as disclosed herein oriented along a feminine sanitary napkin manufacturing line at predetermined positions as necessary, with sharp and square side, leading and trailing edges.

Figure 17:
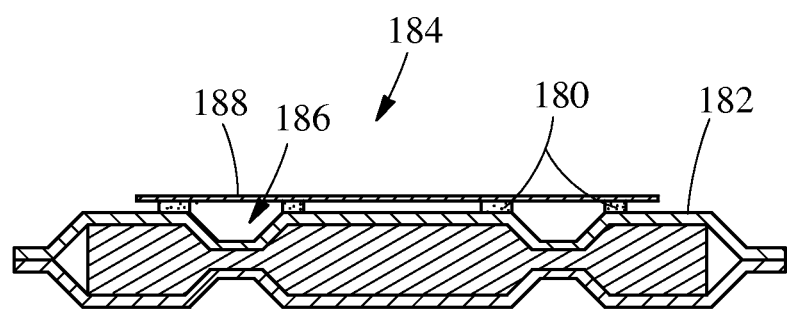
FIG. 17 is a view of a cross-section of a feminine sanitary napkin.
Figure 18:
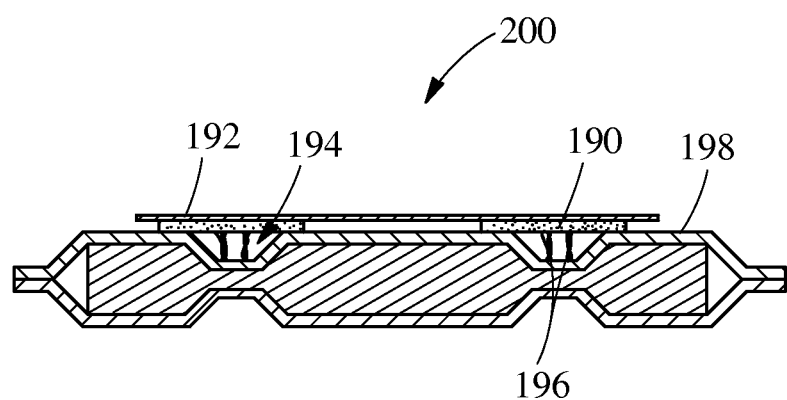
FIG. 18 is a view of a cross-section of a feminine sanitary napkin.

FIGS. 17 and 18 are cross-sections of feminine sanitary napkins in the same position as shown in FIGS. 15 and 16; and illustrate adhesive applications that do not provide the benefits of the present invention. When a contact method of adhesive application, such as using a slot coat applicator, roller or brush, is used to apply adhesive 180 to a backsheet 182 of a feminine sanitary napkin 184, as shown in FIG. 16, the adhesive is not applied to the recessed areas of a depression region 186. This inadequate transfer of adhesive from the release paper to the backsheet increases the likelihood of stringing and residue, potentially transferring adhesive to unintended surfaces, such as a user's panties or hands.

When adhesive is first applied to release paper using a slot coat applicator, roller or brush, and then the release paper is operatively attached to a backsheet, as shown in FIG. 18, the adhesive 190 present on the release paper 192 does not come into direct contact with the recessed portion of a depression region 194. The adhesive 190 present on the release paper 192 forms strings 196 of adhesive 190 in the gap between the release paper 192 and the depression region 194 present in the backsheet 198 of the feminine sanitary napkin 200. During use, when the release paper 192 is separated from the backsheet 198 the strings 196 remain attached to both the release paper 192 and the depression region 194. The dual attachment causes the strings 196 of adhesive to stretch. The stretched strings of adhesive can then attach to unintended surfaces they contact complicating placement of the feminine sanitary napkin and increasing clean-up.

EXAMPLES

Release paper was examined to determine if adhesive remained attached to the release paper following its removal from a feminine sanitary napkin.

Example 1

Sample Preparation

Sample testing was done at room temperature and at standard pressure and humidity.

Figure 19:
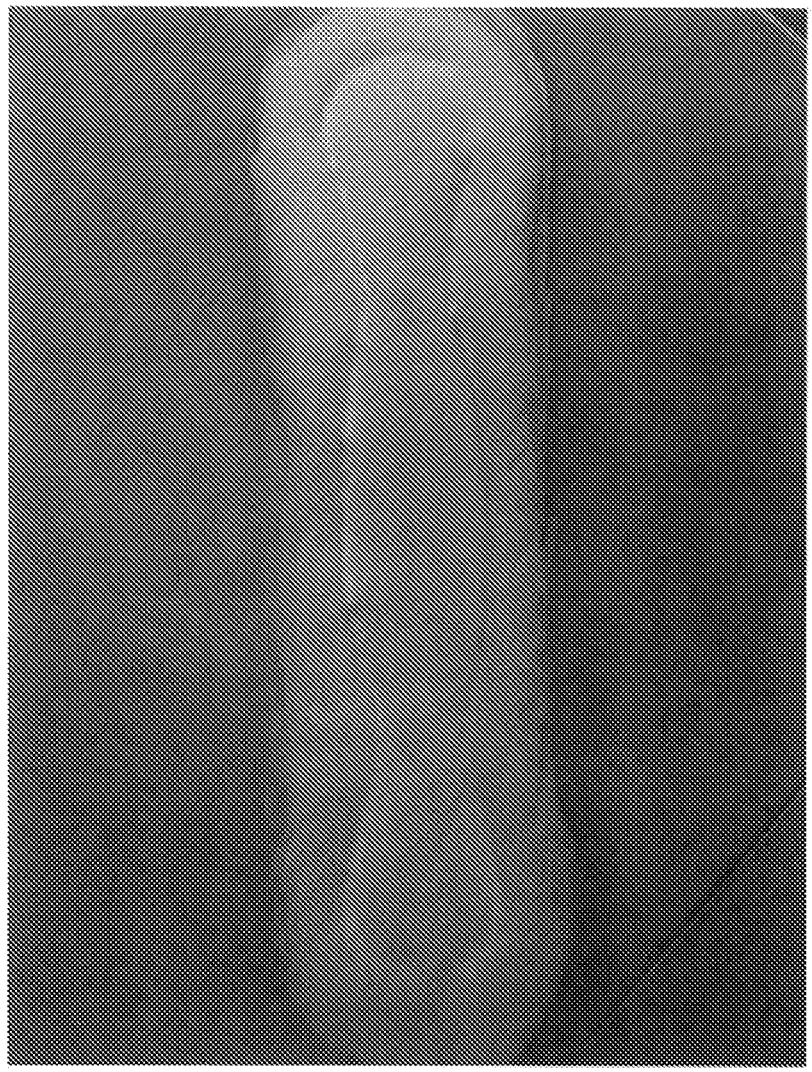
FIG. 19 is a picture of a feminine sanitary napkin.

Samples were prepared by the method described herein. Specifically the samples were ALWAYS® Maxi Pads that were embossed prior to having a polypropylene backsheet attached. An ALWAYS® Maxi Pad was embossed with the embossment region shown in FIG. 19 so that the body facing surface (topsheet) had an average side embossment depth of 5.5 mm and an average end depth of 2.7. The garment facing surface (backsheet) of an ALWAYS® Maxi Pad had an average side depression region depth of 2.6 mm and an average end depression depth of 2.8 mm.

For contact application of adhesive to release paper—Adhesive—EASYMELT® 34-689B from National Starch & Chemical Co., Bridgewater, N.J.; in an amount of 15 grams per square meter (gsm), was applied using an EP 11 Slot Applicator, Nordson Corp., Westlake, Ohio to release paper at a temperature of between 155° C. and 160° C. in two 18 mm wide rectangular shaped patterns spaced 13 mm apart, and having a length (as measured in the MD) that is 7 mm shorter in both the front and rear ends than the applied release paper Immediately after adhesive application the release paper was attached to a feminine sanitary napkin. The release paper used was silicone based release paper RP MONDI 35 gsm 54 mm (width) unprinted (Mondi plc, Addleston Surrey, UK) was cut to length using a cut and slip anvil. The release paper length extended 7 mm past the front end of the adhesive pattern and 7 mm past the rear end of the adhesive pattern as measured in the MD. Following attachment of the release paper, the adhesive was allowed to set for one hour before the release paper was removed.

For non-contact application of adhesive to a backsheet—Adhesive—EASYMELT® 34-689B from National Starch & Chemical Co., Bridgewater, N.J.; in an amount of 15 gsm, was applied using a Control Coat Applicator, Nordson Corp., Westlake, Ohio, to the backsheet of a feminine sanitary napkin at a temperature of between 155° C. and 160° C. in two 18 mm wide rectangular shaped patterns spaced 13 mm apart, and having a length (as measured in the MD) that is 7 mm shorter in both the front and rear ends than the applied release paper. Immediately after adhesive application the release paper was attached to a feminine sanitary napkin. The release paper used was silicone based release paper RP MONDI 35 gsm 54 mm (width) unprinted (Mondi plc, Addleston Surrey, UK) was cut to length using a cut and slip anvil. The release paper length extended 7 mm past the front end of the adhesive pattern and 7 mm past the rear end of the adhesive pattern as measured in the MD. Following application, the adhesive was allowed to set for one hour before the release paper was removed.

Sample Testing

For removal of the release paper a sample ALWAYS® Maxi Pad was held in one hand and the release paper was held in the other hand. The release paper was then removed at a speed a normal user would use. The direction in which the release paper was peeled from the ALWAYS® Maxi Pad did not affect the results. The release paper was then observed for the presence of adhesive.

Figure 20:
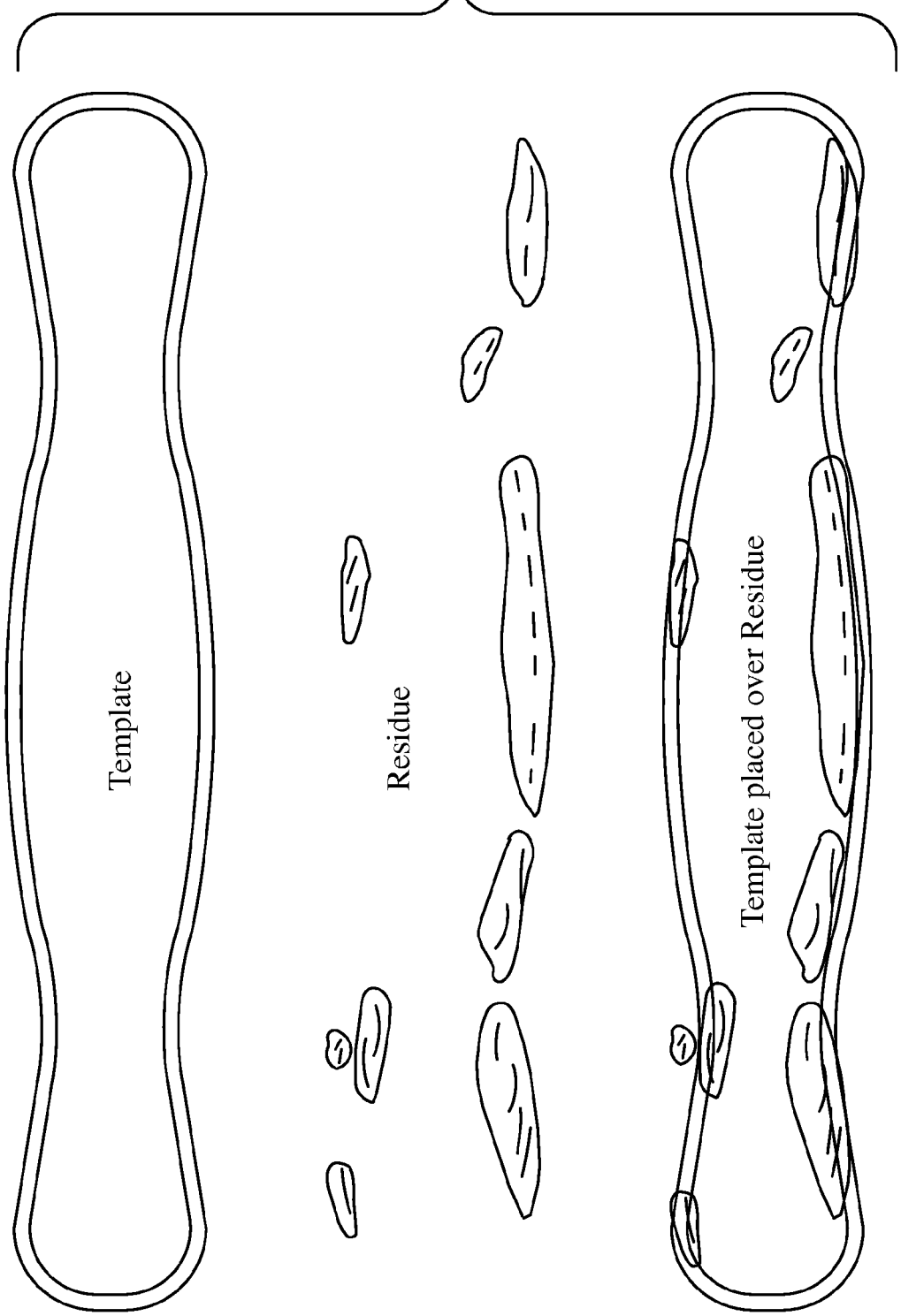
FIG. 20 is a series of pictures showing release paper.

As shown in FIG. 20, samples were considered to have failed the test if the following was observed after removal of the release paper: adhesive residue in the form of three or more adhesive globules or strings on the release paper having an average diameter of 4 mm or greater following the release paper's removal. Stringing includes adhesive that stays attached to both the backsheet and release paper following removal of the release paper and forms adhesive strings between backsheet and release paper.

TABLE 1

| | Contact Application of Adhesive Samples | Non-Contact Application of Adhesive Samples |
|---|---|---|
| Number of Samples Tested | 200 | 200 |
| Presence of three or more adhesive globules or strings | 200 | 0 |

The results show that samples in which the adhesive had been applied to the release paper using a slot applicator (contact method) all of the 200 samples tested had enough adhesive present on the release paper to fail the test. Adhesive present on the release paper results in users not liking the product, as the residual adhesive (either in the form of a string, globule, or both) can get on the user's hands clothes or the absorbent article, in this example a feminine sanitary napkin, interfering with the placement of the feminine sanitary napkin. In contrast all of the samples produced using a non-contact method of adhesive application to the backsheet, as in the present invention, passed the test, in that none of the samples were observed to have three or more adhesive globules or strings present on the release paper. This demonstrates that the adhesive applied using the present invention is applied to and remains in the embossed regions of the samples after the removal of the release paper; in contrast to the adhesive applied using a contact method which is partially removed from the feminine sanitary napkin when the release paper is peeled away.

Example 2

The samples were tested to determine the peel force of adhered cotton to pressure sensitive adhesive. A sample having proper peel force helps ensure the product will stay in place during consumer use, but can be removed without too much difficulty.

Equipment
Cotton Swatch White, 100% die-cut 76 mm×457 mm cotton weave (Style #429-W); available from Testfabrics, Inc., West Pittston, Pa.
Friction Grip Frame Plexiglas plate 80 mm wide by 250 mm long by 2 mm thick, having an open rectangular window 67 mm wide by 175 mm long.
Rigid peel plate smooth steel plate 75 mm wide by 230 mm long by 1.5 mm thick having a raised center portion (about 1 mm as measured from the plate surface) that was slightly smaller than the open rectangular window in the friction grip frame (about 1 mm in each direction) to accommodate, yet grip, the sample.
Compression Weight . . . Metal weight 60 mm wide by 220 mm long, having an area of 132 cm² to provide a mass of 3.50 kg+/−0.07 kgm, so as to cover the adhesive area being tested and apply 26-27 g/sqcm to the sample.
Compressible Polyurethane foam, 25 mm thick, cut to fit the weight length and width dimensions. The hardness of the foam should be between 20 and 80 using a Shore Hardness sponge rubber gauge such as the PTC 302SL from PTC Instruments, LA, Calif. Foam can be ordered from Concord-Renn Company, Cincinnati, Ohio.
Plexiglas plate, fitting the weight length and width dimensions, and having a thickness of 6.4 mm
Transparent Tape (19 mm wide), such as Scotch® Magic™ Tape, from 3M, St. Paul, Minn.
Polyethylene film, 0.02-0.04 mm thick, having length and width dimensions large enough to enclose the polyurethane foam and Plexiglas plate.

Figure 21:
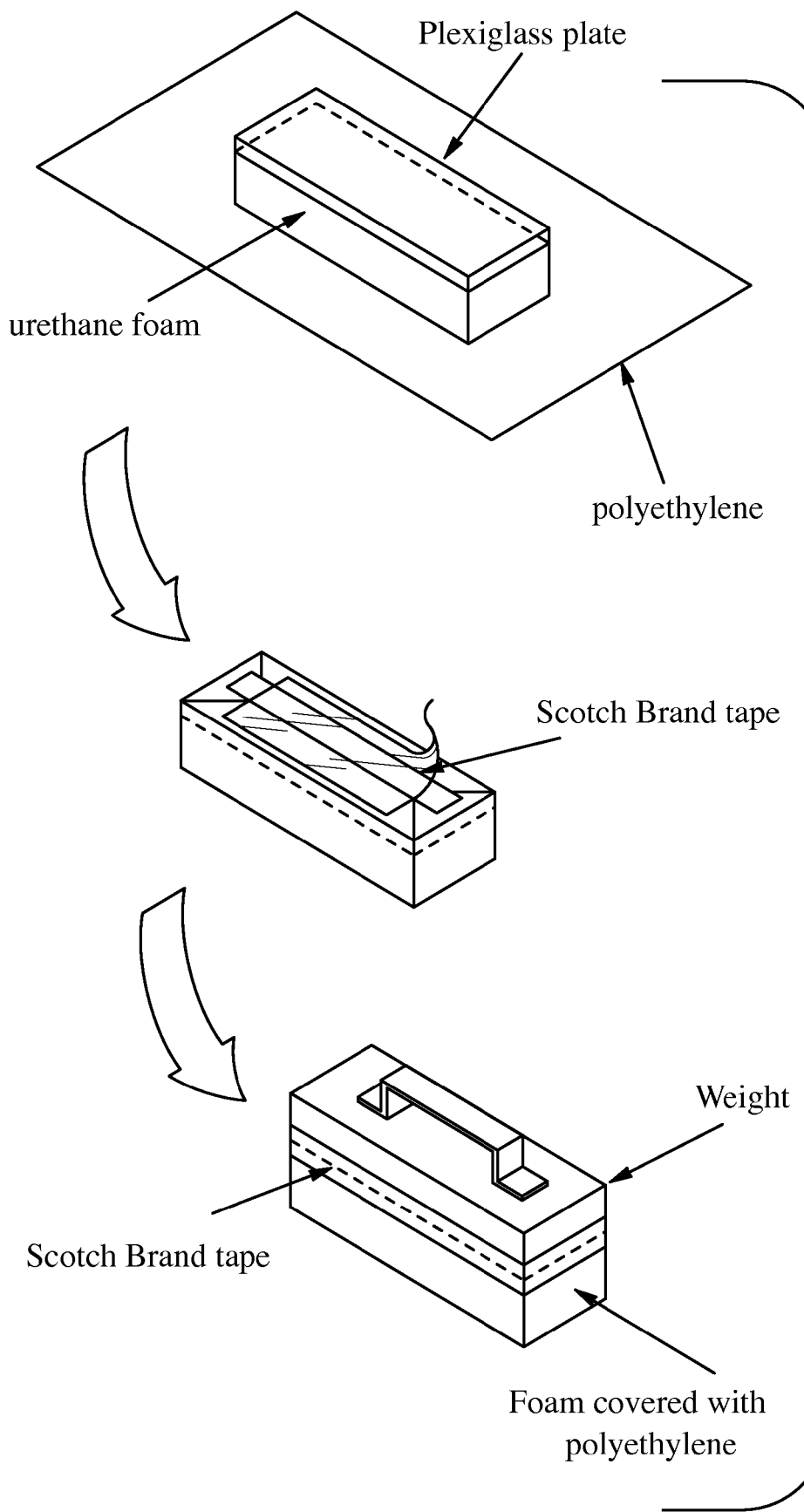
FIG. 21 is a diagram showing the assembly of a compression weight.

Assembly of the compression weight: (See FIG. 21)
1. Polyethylene film was laid on a flat surface.
2. Urethane Foam was positioned on top of the polyethylene film so that the long sides of the foam are parallel with the long sides of the polyethylene film
3. Plexiglas plate was placed on top of the urethane foam.
4. Polyethylene film was folded up over the urethane foam and secured to the Plexiglas plate using transparent tape.
5. The four corners of the urethane foam/Plexiglas plate were aligned with the four corners of the compression weight; with urethane foam side positioned away from the metal surface.
6. Urethane foam/Plexiglas plate was secured to the compression weight using transparent tape.

Tensile Tester . . . MTS Alliance RT-1 Frame; with load cell capacity of 10-100 Newtons (N), available from MTS Systems Corporation, Eden Prairie, Minn.
Tensile Tester Settings
Set the tensile tester to the following values:

| Test Speed* | 1016 mm/min |
| Grip to Grip separation | 250 mm |
| Pre loading | 0 |
| Pre-test path "LB" | 58 mm |
| Test path "LM" | 170 mm |
| Break Detector | 0 |
| Measure Variable | $F_{avg}$ in "LM" |
| Sampling Frequency | 50 Hz |

Sample Preparation
Sample testing is done at room temperature and at standard pressure and humidity.

Samples were prepared by the method described herein. Specifically the samples were ALWAYS® Maxi Pads that were embossed prior to having a polypropylene backsheet attached. An ALWAYS® Maxi Pad was embossed with the embossment region shown in FIG. 19 so that the body facing surface (topsheet) had an average side embossment depth of 5.5 mm and an average end depth of 2.7. The garment facing surface (backsheet) of an ALWAYS® Maxi Pad had an average side depression region depth of 2.6 mm and an average end depression depth of 2.8 mm.

For contact application of adhesive to release paper—Adhesive—EASYMELT® 34-689B from National Starch & Chemical Co., Bridgewater, N.J.; in an amount of 15 gsm, was applied using an EP 11 Slot Applicator, Nordson Corp., Westlake, Ohio to release paper at a temperature of between 155° C. and 160° C. in two 18 mm wide rectangular shaped patterns spaced 13 mm apart, and having a length (as measured in the MD) that is 7 mm shorter in both the front and rear ends than the applied release paper. Immediately after adhesive application the release paper was attached to a feminine sanitary napkin. The release paper used was silicone based release paper RP MONDI 35 gsm 54 mm (width) unprinted (Mondi plc, Addleston Surrey, UK) was cut to length using a cut and slip anvil. The release paper length extended 7 mm past the front end of the adhesive pattern and 7 mm past the rear end of the adhesive pattern as measured in the MD. Following attachment of the release paper, the adhesive was allowed to set for one hour before the release paper was removed.

For non-contact application of adhesive to a backsheet—Adhesive—EASYMELT® 34-689B from National Starch & Chemical Co., Bridgewater, N.J.; in an amount of 15 gsm, was applied using a Control Coat Applicator, Nordson Corp., Westlake, Ohio, to the backsheet of a feminine sanitary napkin at a temperature of between 155° C. and 160° C. in two 18 mm wide rectangular shaped patterns spaced 13 mm apart, and having a length (as measured in the MD) that is 7 mm shorter in both the front and rear ends than the applied release paper. Immediately after adhesive application the release paper was attached to a feminine sanitary napkin. The release paper used was silicone based release paper RP MONDI 35 gsm 54 mm (width) unprinted (Mondi plc, Addleston Surrey, UK) was cut to length using a cut and slip anvil. The release paper length extended 7 mm past the front end of the adhesive pattern and 7 mm past the rear end of the adhesive pattern as measured in the MD. Following application, the adhesive was allowed to set for one hour before the release paper was removed.

Figure 22E:
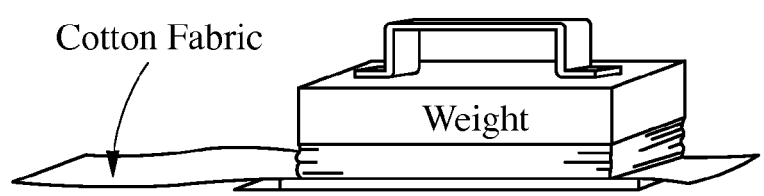
Figure 22D:
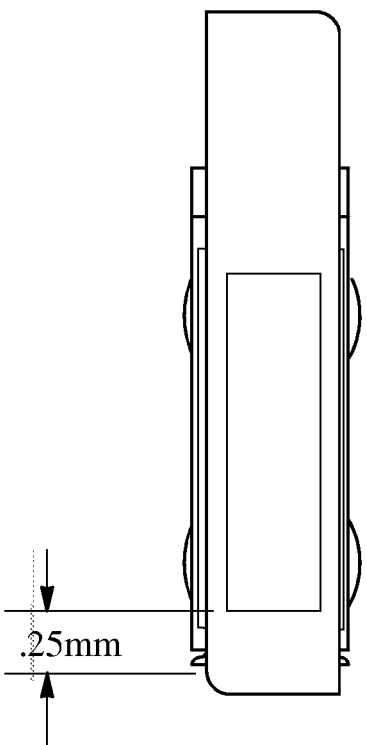
Figure 22F:
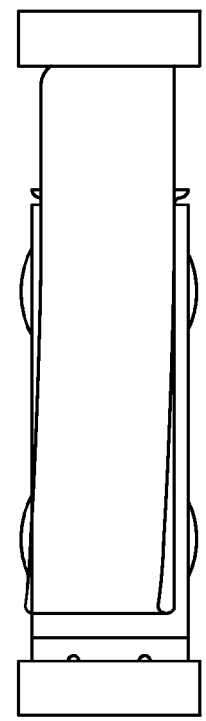

Sample Preparation (Shown in FIGS. 22 and 22A-22F)
1. A sample was placed with the adhesive side up; onto the rigid peel plate (FIG. 22A).
2. The sample was secured on the rigid peel plate by placing the friction grip frame over the sample (FIG. 22B).

3. The release paper was then peeled from the adhesive (FIG. 22C).
4. Within five minutes following removal of the release paper a cotton swatch was laid over the exposed adhesive. One end of the cotton swatch extended past the top or bottom edge of the adhesive by about 25 mm (cotton swatch leading end) (FIG. 22D).
5. The compression weight was then placed on the cotton swatch so that the compression weight completely covered the adhesive area (FIG. 22E). Force was not used to apply the compression weight to the cotton swatch, rather the compression weight was placed on the cotton swatch without any pressure being applied by the tester's hand; as deviations in how the compression weight is placed from sample to sample can cause variations in results, for example dropping the compression weight down onto the sample results in much higher compression forces, and higher resulting peel force. The compression weight was left on the sample for 30 seconds (±2 s).
6. The weight was gently removed without adding any extra pressure to the sample while lifting the compression weight.

Sample Testing

Samples were tested within 1 minute after the compression weight was removed.
1. The load cell was tared (zeroed)
2. The top end of the rigid peel plate was placed into the lower clamp of the tensile tester and the tail end of the cotton swatch was placed into the upper clamp with the load cell.
3. The rigid peel plate and the cotton swatch were adjusted in the upper and lower clamps, so that the cotton swatch is lined up with the top or bottom edge of the adhesive pattern (peel line) (FIG. 22F).
4. The cotton swatch was checked to ensure it was not loose before fixing it into the upper clamp and the peel line is evenly centered and parallel to the upper and lower clamps. There was 0.1 N of tension on the cotton swatch at the start of the test. This initial tension was not tared (zeroed).
5. The tensile tester was started and the upper clamp (FIG. 22F) began to pull the cotton swatch (Pre-test path "LB"). At 58 mm into the test full data collection was started and ended at 170 mm (Test path "LM"). The data collected between the 58 mm mark and the 170 mm mark was averaged for each pad tested, and is shown in TABLES 2 and 3.

TABLE 2

Contact Application of Adhesive Samples

| Sample | Avg Load in grams of force (gf) | Peak Load in grams of force (gf) |
| --- | --- | --- |
| 1 | 223.1 | 462.7 |
| 2 | 260.8 | 590.5 |
| 3 | 247.7 | 568. |
| 4 | 306.1 | 889.1 |
| 5 | 353 | 925.3 |
| Avg | 278.1 | 687.1 |
| Std Deviation | 51.5 | 206.9 |

TABLE 3

Non-Contact Application of Adhesive Samples

| | Avg Load (gf) | Peak Load (gf) |
| --- | --- | --- |
| 6 | 294.3 | 573 |
| 7 | 305.8 | 520.3 |
| 8 | 274.3 | 514.2 |
| 9 | 306.5 | 541.9 |
| 10 | 352.7 | 574.4 |
| Avg | 306.7 | 544.7 |
| Std Deviation | 28.8 | 28.3 |

The results in TABLE 2 and TABLE 3 show that the peel force (amount of force used to remove the cotton swatch from the adhesive) is more consistent when adhesive is applied using a non-contact method as compared to a contact method of adhesive application. The consistency of the peel force is dramatically better for samples prepared using a non-contact adhesive application (samples 6-10) as compared to samples prepared using a contact adhesive application (samples 1-5)—for samples 6-10 the standard deviation for Average Load in Grams of Force was 28.8 gf and the standard deviation for Peak Load in Grams of Force was 28.3 gf; as compared to samples 1-5 that had a standard deviation for Average Load in Grams of Force of 51.5 gf and a standard deviation for Peak Load in Grams of Force of 206.9 gf. Consistency of peel force is an important element of adhesion performance for an adhesive. If the peel force is too low, then the ability of the absorbent article, in this example a feminine sanitary napkin, to stay in place (attached to the cotton swatch) is compromised; if the peel force is too high, it is difficult to remove the feminine sanitary napkin from the cotton swatch. Reducing the variability in peel force significantly reduces the probability of having feminine sanitary napkins at either problematic extreme. And the reduction in peel force variability is illustrated in the comparatively low standards of deviation (28.8 gf and 28.3 gf) observed in samples 6-10 as compared to the comparatively high standards of deviation (51.5 gf and 206.9 gf) observed in samples 1-5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for embossing an absorbent article comprising the steps of:
providing a topsheet;
providing an absorbent core having a garment facing side and a body facing side and positioning the body facing side of the absorbent core on the topsheet;
operatively contacting the garment facing side of the absorbent core with a segmented anvil member and the topsheet with an embossment member of a rotary embossing device to form an embossment region in at least a portion of the topsheet and body facing side of the absorbent core and a depression region in the garment facing side of the absorbent core;
thereafter contacting a substantially liquid impervious backsheet directly with the garment facing side of the absorbent core wherein a portion of the backsheet protrudes into the depression region in the garment facing side of the absorbent core, and
applying adhesive in a pattern to the backsheet using a non-contact die means.

2. A method for embossing an absorbent article comprising the steps of:
providing a topsheet;
providing an absorbent core having a garment facing side and a body facing side and positioning the body facing side of the absorbent core on the topsheet;
moving the topsheet and absorbent core in a machine direction;
operatively contacting the garment facing side of the absorbent core with a segmented anvil member and the topsheet with an embossing member of a rotary embossing device to form an embossment region in at least a portion of the topsheet and body facing side of the absorbent core and a depression region in the garment facing side of the absorbent core;
contacting a backsheet directly with the garment facing side of the absorbent core having a depression region, wherein the backsheet is substantially liquid impervious;
applying adhesive in a pattern to the backsheet using a non-contact die means; and
operatively attaching a release paper to the backsheet;
wherein the absorbent article is a unitary article comprising at least the topsheet, the absorbent core, the backsheet, the adhesive, and the release paper.

3. The method of claim 2, wherein the segmented anvil member comprises two or more segmented sections and each segmented section includes two or more movable portions such that the movable portions reduce the distance between an embossment member and the segmented anvil member.

4. The method of claim 2, wherein the embossing member has a height that is from about 2 mm to about 12 mm.

5. The method of claim 2, wherein the embossing member applies a force value of about $1 \times 10^5$ N/m to about $3 \times 10^7$ N/m to the embossment region.

6. The method of claim 2, wherein the embossing member forms an embossment region having a depth of about 20% to about 75% of the thickness of the absorbent article.

7. The method of claim 2, wherein the embossing member forms a depression region having a depth of about 15% to about 75% of the thickness of the absorbent article.

8. The method of claim 2, wherein the adhesive is a meltblown adhesive.

9. The method of claim 2, wherein the adhesive pattern has a defined surface area, the adhesive covering at least about 80% of the defined surface area.

10. The method of claim 2, wherein the adhesive pattern has a width and defined surface area, the adhesive covering at least about 90% of the defined surface area.

11. The method of claim 10, wherein the adhesive pattern has an edge definition variation within 0 mm to about 2 mm of the pattern width, when forming within a forming distance of about 8 mm to about 25 mm.

12. The method of claim 2, wherein a portion of the backsheet protrudes into the depression region in the garment facing side of the absorbent core.

13. A method for embossing an absorbent article comprising the steps of:
providing a topsheet;
providing an absorbent core having a garment facing side and a body facing side and positioning the body facing side of the absorbent core on the topsheet;
moving the topsheet and absorbent core in a machine direction;
operatively contacting the garment facing side of the absorbent core with a segmented anvil member and the topsheet with an embossment member of a rotary embossing device to form an embossment region in at least a portion of the topsheet and body facing side of the absorbent core and a depression region in the garment facing side of the absorbent core;
contacting a backsheet directly with the garment facing side of the absorbent core having a depression region, wherein the backsheet is substantially liquid impervious;
applying adhesive in a pattern to the backsheet using a non-contact die means;
wherein the application of adhesive comprises the steps of:
extruding adhesive from an extrusion outlet;
impinging a flow of air from the extrusion outlet at an angle unto the extruding adhesive;
depositing extruded adhesive onto the backsheet; and
operatively attaching a release paper to the backsheet;
wherein the absorbent article is a unitary article comprising at least the topsheet, the absorbent core, the backsheet, the adhesive, and the release paper.

14. The method of claim 13, wherein the segmented anvil member comprises two or more segmented sections and each segmented section includes two or more movable portions such that the movable portions reduce the distance between an embossment member and the segmented anvil member.

15. The method of claim 13, wherein the application of adhesive also comprises the step of starting and stopping the extrusion of adhesive to produce discrete adhesive patterns.

16. The method of claim 13, wherein the embossing member has a height that is from about 2 mm to about 12 mm.

17. The method of claim 13, wherein the embossing member applies a force value of about $1 \times 10^5$ N/m to about $3 \times 10^7$ N/m to the embossment region.

18. The method of claim 13, wherein the embossing member forms a depression region having a depth of about 15% to about 75% of the thickness of the absorbent article.

19. The method of claim 13, wherein the adhesive is a meltblown adhesive.

20. The method of claim 13, wherein the adhesive pattern has a defined surface area, the adhesive covering at least about 80% of the defined surface area.

21. The method of claim 13, wherein the adhesive pattern has a width and defined surface area, the adhesive covering at least about 90% of the defined surface area.

22. The method of claim 21, wherein the adhesive pattern has an edge definition variation within 0 mm to about 2 mm of the pattern width, when forming within a forming distance of about 8 mm to about 25 mm.

23. The method of claim 13, wherein a portion of the backsheet protrudes into the depression region in the garment facing side of the absorbent core.

* * * * *